(12) United States Patent
Bockelman et al.

(10) Patent No.: US 10,373,709 B2
(45) Date of Patent: Aug. 6, 2019

(54) FRAMEWORK FOR MODELING A CLINICAL TRIAL STUDY USING A CROSS-OVER TREATMENT DESIGN

(71) Applicant: Oracle International Corporation, Redwood Shores, CA (US)

(72) Inventors: Scott Andrew Bockelman, Glen Ellyn, IL (US); John Caron, Carol Stream, IL (US); Naresh Baliga, Santa Clara, CA (US); Leyla Badakhshanian, Downers Grove, IL (US)

(73) Assignee: ORACLE INTERNATIONAL CORPORATION, Redwood Shores, CA (US)

( * ) Notice: Subject to any disclaimer, the term of this patent is extended or adjusted under 35 U.S.C. 154(b) by 876 days.

(21) Appl. No.: 13/875,570

(22) Filed: May 2, 2013

(65) Prior Publication Data

US 2014/0330572 A1  Nov. 6, 2014

(51) Int. Cl.
*G06F 19/00* (2018.01)
*G16H 10/20* (2018.01)

(52) U.S. Cl.
CPC .................................. *G16H 10/20* (2018.01)

(58) Field of Classification Search
CPC ........ A61B 5/7275; G06N 3/08; G06N 3/105; G06Q 50/22; G06Q 50/24; G06Q 10/00; G16H 50/20; G16H 50/70; G16H 20/10; G16H 50/50; G16H 10/20; G06F 16/285; G06F 17/18; G06F 16/248
See application file for complete search history.

(56) References Cited

U.S. PATENT DOCUMENTS

2009/0093995 A1* 4/2009 Woosley et al. ............... 702/182
2013/0006649 A1* 1/2013 Rangadass et al. ............... 705/2

* cited by examiner

*Primary Examiner* — Maroun P Kanaan
(74) *Attorney, Agent, or Firm* — Kraguljac Law Group, LLC

(57) ABSTRACT

The present disclosure provides for modeling a clinical trial study, which may implement a cross-over design. A plurality of treatments is generated for a clinical trial study, based on a first subset of operational parameters. A plurality of sequences is also generated for the clinical trial study, based on a second subset of the operational parameters. Each sequence of the plurality of sequences comprises a combination of ones of the plurality of treatments. A plurality of subject groups is assigned to the plurality of sequences, where one subject group of the plurality of subject groups is respectively assigned to one sequence of the plurality of sequences. The one sequence is administered to subjects of the one subject group during the clinical trial study.

18 Claims, 15 Drawing Sheets

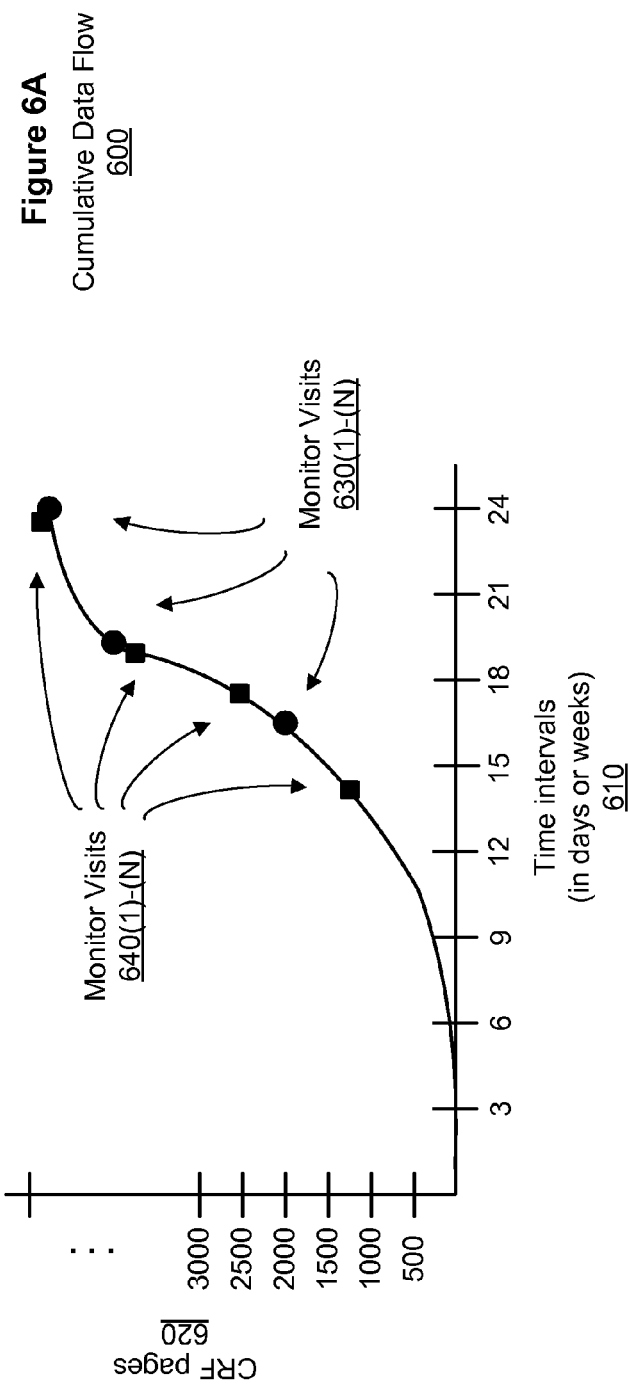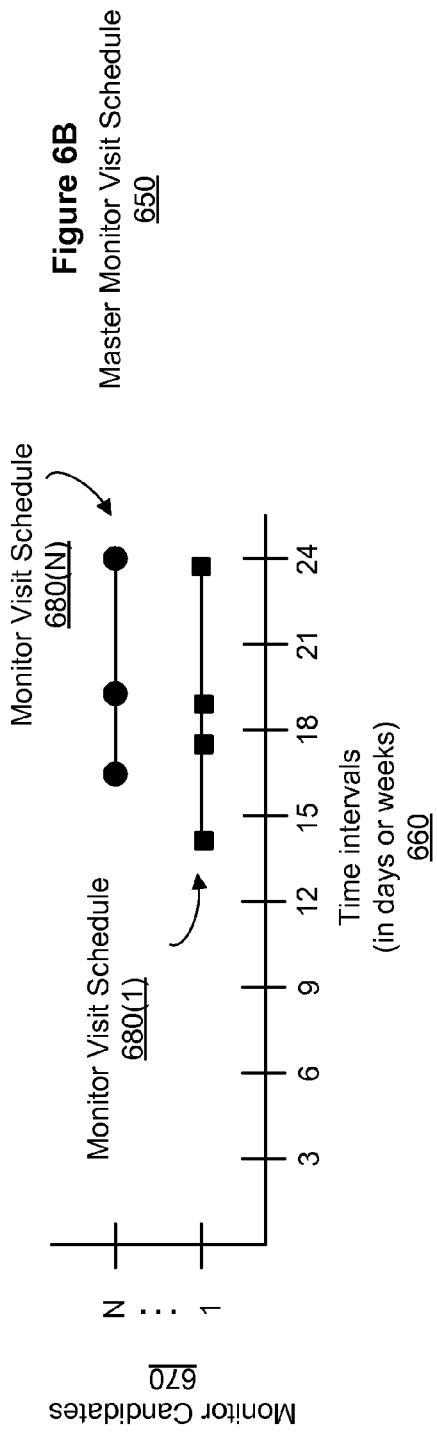

| Resource Demand Forecast 255 | | | | | | |
|---|---|---|---|---|---|---|
| Resources 700 Tasks 705 | Unit Of Measure 710 | Number Of Units 715 | Unit Hours 720 | Unit Cost 725 | Extended Unit Hours 730 | Extended Unit Cost 735 |
| 700(1) Monitor 705(1) Travel to investigator sites 705(2) Collect and verify CRF data | Monitor Visits | 100 | 8.0 | $2,551.57 | 400.0 | $227,578.50 |
| 700(2) Senior Programmer 705(3) Develop data entry screen 705(4) Conduct quality control on data entry screen 705(5) Program the data entry screen | Screens | 72 | 9.0 | $1,668.08 | 648.0 | $119,957.76 |
| 700(3) Program Analyst 705(6) Design and document database 705(7) Define attributes for the database 705(8) Program the database | Database | 1 | 786.6 | $122,956.56 | 786.6 | $122,956.56 |
| 700(4) Medical writer 705(9) Draft report 705(10) Conduct literature searches 705(11) Conduct quality control check of summary report results 705(12) Discuss summary of relevant efficacy and safety | Draft Report | 1 | 304.8 | $52,310.05 | 304.8 | $52,310.05 |

Figure 7

| Tasks 805 | Unit Of Measure 810 | Effort Forecast 260 ||||| 
| | | Number Of Units 815 | Unit Hours 820 | Unit Cost 825 | Extended Unit Hours 830 | Extended Unit Cost 835 |
| --- | --- | --- | --- | --- | --- | --- |
| 805(1) Project Initiated | Projection Initiation | 1 | 273.3 | $60,162.29 | 273 | $60,162 |
| 805(2) Study Setup | Centralized Study Setup Tasks | 1 | 307.4 | $50,759.95 | 307 | $50,760 |
| 805(3) Study Setup-Location | Decentralized Study Setup Tasks | 4 | 46.0 | $7,711.95 | 184 | $30,848 |
| 805(4) Unique CRF Page Developed | CRF Development | 24 | 14.8 | $2,935.58 | 355 | $70,454 |
| 805(5) CRF Book Printed | CRF Printing | 0 | 0.0 | $0.00 | 0 | $0 |
| 805(6) Meetings–Kickoff | Kickoff Meetings | 1 | 62.0 | $16,006.56 | 62 | $16,007 |
| 805(7) Meetings–Investigator | Investigator Meetings | 1 | 280.0 | $56,600.07 | 280 | $56,600 |
| 805(8) Meetings–Face/Face | Face Meetings | 1 | 82.0 | $20,404.68 | 82 | $20,405 |
| 805(9) Meetings–Teleconf. | Tele Meetings | 132 | 3.5 | $762.97 | 462 | $100,712 |
| 805(10) Meetings–Team | Team Meetings | 132 | 6.5 | $1,591.55 | 858 | $210,085 |
| 805(11) Site Identified By Vendor | Site IDs | 80 | 4.1 | $772.61 | 328 | $61,809 |
| 805(12) Pre-study Site Visit | Visits | 88 | 16.8 | $3,169.86 | 1478 | $278,948 |

Figure 8

Budget Forecast
265

| Tasks 905 | Task Monthly Total 915(1) | Task Monthly Total 915(2) | Task Monthly Total 915(3) | Task Monthly Total 915(4) | Task Monthly Total 915(5) | Task Total 925 |
|---|---|---|---|---|---|---|
| 905(1) Project Initiated | $20,495 | $19,834 | $19,833 | $0 | $0 | ⋮ | $60,162 |
| 905(2) Study Setup | $17,292 | $16,734 | $16,734 | $0 | $0 | ⋮ | $50,760 |
| 905(3) Study Setup Per-Location | $7,008 | $6,780 | $6,932 | $4,727 | $4,225 | ⋮ | $30,484 |
| 905(4) Unique CRF Page Developed | $18,902 | $51,552 | $0 | $0 | $0 | ⋮ | $70,454 |
| 905(5) CRF Book Printed | $0 | $0 | $0 | $0 | $0 | | $0 |
| 905(6) Meetings – Kickoff | $16,007 | $0 | $0 | $0 | $0 | ⋮ | $16,007 |
| 905(7) Meetings – Investigator | $0 | $0 | $56,600 | $0 | $0 | ⋮ | $56,600 |
| 905(8) Meetings - Face to Face | $0 | $0 | $20,405 | $0 | $0 | ⋮ | $20,405 |
| 905(9) Meetings – Teleconference | $3,815 | $3,052 | $3,815 | $3,052 | $3,052 | ⋮ | $26,704 |
| Study Monthly Total 920 | $417,959 | $392,525 | $497,276 | $115,355 | $110,450 | ⋮ | $2,779,445 |

Figure 9

Timeline Forecast
270

| Milestones 1005 | Date 1010 |
|---|---|
| 1005(1) Project Activity Start Date | May 1, 2012 |
| 1005(2) First Site Approved | June 12, 2012 |
| 1005(3) Investigator Meeting | July 24, 2012 |
| 1005(4) Drug Available to First Site | July 26, 2012 |
| 1005(5) First Subject/Patient In | July 31, 2012 |
| 1005(6) Agreement on Statistical Analysis Plan | November 28, 2012 |
| 1005(7) Last Site Approved | December 3, 2012 |
| 1005(8) Last Subject/Patient In | July 29, 2013 |
| 1005(9) Last Subject Patient Observation | July 29, 2013 |
| 1005(10) Last Data Query Resolved | August 8, 2014 |
| 1005(11) Database Lock | August 10, 2014 |
| 1005(12) Final Report | November 8, 2014 |
| Study Duration (approx. months) 1015 | 30.2 |

Figure 10

FRAMEWORK FOR MODELING A CLINICAL TRIAL STUDY USING A CROSS-OVER TREATMENT DESIGN

FIELD OF THE INVENTION

This invention relates to clinical trial studies, and more particularly, to modeling clinical trial studies that implement a cross-over treatment design.

BACKGROUND OF THE INVENTION

Before a drug can be marketed or sold in a given country, the drug must be approved by the country's ministry of health or similar regulatory body (for example, the United States Federal Drug Administration). In order to gain such approval, pharmaceutical companies sponsor a number of clinical trial studies that are designed to determine the efficacy and safety of the drug. Pharmaceutical companies often make decisions about which clinical trial studies to sponsor based on cost estimates of the clinical trial studies. Implementing a clinical trial study can be quite complex and costs can be difficult to estimate, especially if the costs are determined using an inaccurate model of the clinical trial study.

SUMMARY OF THE INVENTION

The present disclosure provides for modeling a clinical trial study, which may implement a cross-over design. A plurality of treatments is generated for a clinical trial study, based on a first subset of operational parameters. A plurality of sequences is also generated for the clinical trial study, based on a second subset of the operational parameters. Each sequence of the plurality of sequences comprises a combination of ones of the plurality of treatments. A plurality of subject groups is assigned to the plurality of sequences, where one subject group of the plurality of subject groups is respectively assigned to one sequence of the plurality of sequences. The one sequence is administered to subjects of the one subject group during the clinical trial study.

BRIEF DESCRIPTION OF THE DRAWINGS

The present invention may be better understood, and its numerous objects, features and advantages made apparent to those skilled in the art by referencing the accompanying drawings.

FIG. 6A is a simplified graphical representation illustrating elements of an example data flow, according to one embodiment.

FIG. 6B is a simplified graphical representation illustrating elements of an example master monitor visit schedule, according to one embodiment.

FIG. 7 is a simplified block diagram illustrating elements of an example resource demand forecast, according to one embodiment.

FIG. 8 is a simplified block diagram illustrating elements of an example effort forecast, according to one embodiment.

FIG. 9 is a simplified block diagram illustrating elements of an example budget forecast, according to one embodiment.

FIG. 10 is a simplified block diagram illustrating elements of an example timeline forecast, according to one embodiment.

Figure 1:
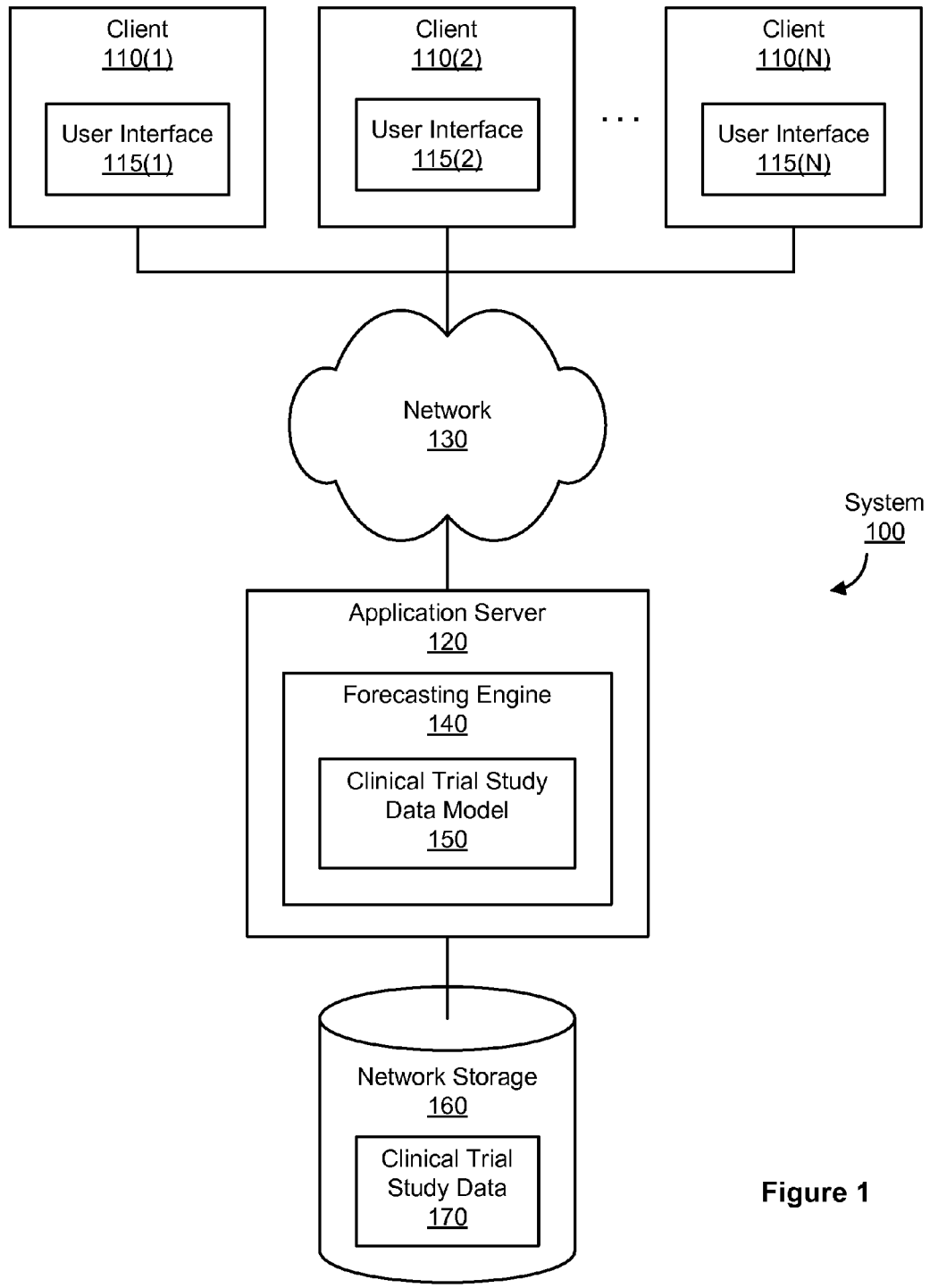
FIG. 1 is a simplified block diagram illustrating components of an example system in which the present disclosure can be implemented, according to one embodiment.

While the present disclosure is susceptible to various modifications and alternative forms, specific embodiments of the present disclosure are provided as examples in the drawings and detailed description. It should be understood that the drawings and detailed description are not intended to limit the present disclosure to the particular form disclosed. Instead, the intention is to cover all modifications, equivalents, and alternatives falling within the spirit and scope of the present disclosure as defined by the appended claims.

DETAILED DESCRIPTION

Clinical trial studies are required in order to collect result data submissible to regulatory bodies (e.g., ministry of health, US Federal Drug Administration) that will approve or deny the use, marketing, advertising, sale, and any claim made about a medicinal drug or medical device (also referred to as a treatment). A clinical trial study (or more simply, study) usually involves several phases, such as a setup phase (e.g., acquiring the needed approval to perform the study), an enrollment phase (e.g., enrolling people to participate in the study), a testing phase (e.g., testing one or more treatments during the study), and an analysis phase (e.g., analyzing the data collected during the testing phase to produce a final report about the treatment). Typically, a sponsor (e.g., a pharmaceutical company or medical device manufacturer) funds the study and hires an investigator to perform the study. An investigator is a doctor, university, or other such entity that performs or manages the study, where employees of the investigator (e.g., nurses, interns, doctors) enroll subjects (e.g., patients or volunteers), give the treatment being tested to the subjects, and record data about the subjects in a case report form (CRF).

Once generated, the CRF data needs to be collected and properly verified in order to be used as result data of the study, which can be analyzed and used for the final report. A monitor is assigned the tasks of collecting the CRF data recorded during the testing phase and verifying the CRF data against other source data (e.g., compare CRF data with a subject's chart) to ensure that a real person in the study is generating the CRF data, as well as to resolve any discrepancies in the CRF data (collectively referred to as monitoring). Investigators can perform monitoring in-house (e.g., assign employees of the investigator to perform monitoring duties), but investigators often outsource monitoring to third parties that act as dedicated monitors. Monitoring is often the most expensive aspect of implementing a clinical trial study, since monitors charge for labor from the moment they leave their home until their return, as well as travel costs and other pass-through costs. Once collected and verified, CRF data can be used as result data and is analyzed by the investigator, who then writes a final report about the findings of the study.

During a clinical trial study, a number of subjects are enrolled to undergo randomized treatment to test a medicinal drug or medical device. While subjects could be traditionally divided into a treated group that receives the treatment (such as receiving or using the medicinal drug or medical device) and a control group that receives the control treatment (such as receiving a placebo or otherwise not receiving or using the medicinal drug or medical device), comparing result data of the subjects is difficult due to variable factors of the subjects, such as age, weight, sex, ethnicity, lifestyle, and the like. Using such an approach, these factors would need to be ruled out or normalized in order to make significant or specific claims about the safety or efficacy of the medicinal drug or medical device being tested. In order to rule out such factors, it would be necessary to recruit large numbers of subjects into the trial, where the result data can later be grouped by subject characteristics to better determine whether the subject characteristics are responsible for certain trends in the result data rather than the drug or device being tested.

Rather than traditionally limit a subject to one treatment, a clinical trial study can implement a cross-over treatment design (also referred to as a cross-over study). In a cross-over study, each subject acts as his or her own control group, which normalizes the result data because the control group is virtually identical to the treated group (because the treated group subjects are the same people as the control group subjects). Cross-over treatment design is especially beneficial to collect statistically meaningful result data when large numbers of subjects are difficult to recruit and where studies are held in smaller subject populations. The subject receives the drug or device being tested for some portion of the study, and then receives the placebo or control treatment during another portion of the study. Thus, a subject will cross over from a treated group to a control group at one or more points during the testing phase of the study, which is referred to as a sequence of treatments.

A cross-over study can be quite complex to implement, requiring a multitude of tasks to complete across various phases of the study. Costs of the study can also be difficult to estimate, especially if the costs are determined using an inaccurate model of the study. The present disclosure provides for a data model of a cross-over study that represents the various sequences of treatments that a subject will receive during a cross-over study, as well as other operational parameters of the cross-over study that can be used to accurately estimate the resources, effort, cost, and time required to implement the study. The data model can also be used to accurately estimate a subject visit schedule and a monitor visit schedule. The aforementioned features, as well as others, are further discussed below.

For example, the cross-over study data model provides a template that can be used to generate a representation of each study (also referred to as a data model object) that a user (e.g., a sponsor, such as a pharmaceutical company) wishes to implement. The user can specify the configuration of a particular cross-over study by specifying particular values of operational parameters, such as specifying a number of treatments that will be administered to a number of subjects during a particular cross-over study. The cross-over study data model describes the different relationships between aspects of a cross-over study, such as the relationships between treatments, sequences, subjects, subject visits, and CRF data. Other information can be estimated using the cross-over study data model, such as estimating a total amount of CRF data recorded during subject visits (or data flow), and estimating a number of monitor visits based on the data flow. This information can be used to estimate, or forecast, the cost of implementing the cross-over study, a list of resources that will be needed during the cross-over study, a list of tasks to be performed by the resources to implement the cross-over study, and an amount of time needed to complete the cross-over study. The operational parameters and other information can be stored in (or associated with) the data model object that represents the particular cross-over study.

FIG. 1 is a simplified block diagram illustrating components of an example system 100 in which the present disclosure can be implemented. In the embodiment shown, system 100 includes one or more client systems 110(1)-(N), an application server 120, a forecasting engine 140 that implements a clinical trial study data model 150 (also referred to as data model 150), a communications network 130, and network storage 160 that stores clinical trial study data 170. Each component is discussed in further detail below.

One or more client systems 110(1)-(N), also referred to collectively herein as client devices 110 and/or clients 110, can each be implemented using, for example, a desktop computer, a laptop computer, a workstation, a server, or the like. An example of one such computing device is described subsequently, in connection with FIG. 12. One or more clients 110(1)-(N) are communicatively coupled with application server 120, such as via a communications network 130. Examples of communications network 130 include a dedicated communication line, a local area network (LAN) utilizing Ethernet, IEEE 802.11x, or some other communications protocol, and a wide area network (WAN), such as the Internet.

Client systems 110(1)-(N) also respectively implement a user interface 115(1)-(N), which is configured to communicate with forecasting engine 140, such as by sending user input to forecasting engine 140 via network 130 and receiving output from forecasting engine 140 via network 130. User interface 115(1)-(N) can each be a graphical user interface (GUI) that implements graphical elements (e.g., visual images, icons, buttons, pointers, etc.) with which a user can interact to provide user input and/or to view a display of forecasting engine output.

Application server 120 (or more simply, server 120) can include one or more physical servers configured to perform a variety of tasks related to modeling of clinical trial studies for system 100. An example computing device that can be used to implement server 120 is described subsequently, in connection with FIG. 12. Server 120 is configured to implement forecasting engine 140 as part of a clinical trial study modeling application, such as Oracle® Health Services ClearTrial (available from Oracle International Corporation of Redwood Shores, Calif.).

Forecasting engine 140 is configured to generate a forecast, or an estimate, of the effort, resources, and cost that would be required to execute a clinical trial study (also referred to herein as a study), where forecasting engine 140 can generate forecasts for multiple studies. Forecasting engine 140 is configured to receive operational parameters (e.g., user input received from user interface 115) that define the scope of a particular clinical trial study. Operational parameters are user-specified values that describe the configuration of a particular clinical trial study, which can also include operational assumptions made by the user. Forecasting engine 140 is configured to generate a data model object for each particular clinical trial study from a clinical trial study data model 150, which acts as a template that describes various aspects of a clinical trial study implementing a cross-over treatment design. Forecasting engine 140 can populate the generated data model object with the operational parameters. Forecasting engine 140 can store the data model object locally (e.g., in a buffer or cache), and can communicate the data model object to network storage 160 for storage as clinical trial study data 170.

Using the operational parameters in conjunction with clinical trial study data model 150, forecasting engine 140 is configured to generate various forecasts (e.g., forecasting engine output) of the clinical trial study, such as an effort forecast, a resource demand forecast, a budget forecast, and a timeline forecast. Forecasting engine 140 is also configured to generate intermediate results (e.g., forecasting engine output), such as a subject visit schedule and a monitor visit schedule. Forecasting engine 140 is discussed in further detail below.

A number of data model objects (which include operational parameters of particular cross-over studies) and other information can be stored in network storage 160 as clinical trial study data 170. For example, clinical trial study data 170 can include resource information, such as a list of default resources, a list of user-specified resources, billing rates of the resources, availability schedules of the resources, a list of tasks associated with each resource, and the like. Clinical trial study data 170 can also include task information, such as a list of default tasks, a list of user-specified tasks, a cost to perform a unit task (e.g., unit cost), a number of hours to perform a unit task (e.g., unit hours), and the like. Clinical trial study data 170 can also include output data generated by forecasting engine 140 that includes various schedules and forecasts, such as a subject visit schedule, a monitor visit schedule, a resource demand forecast, a budget forecast, an effort forecast, a timeline forecast, and the like. Clinical trial study data 170 can also include information associated with a number of data model objects that represent a different cross-over study. For example, each data model object can be associated with a number of schedules and forecasts of the particular cross-over study represented by the data model object. Each data model object can also be associated with default and user-specified information (e.g., resource information and task information), and the like.

Network storage 160 can be implemented as network attached storage (NAS), file servers, storage filers, and/or network shares. Network storage 160 can be implemented as a single storage device or as a collection of storage devices. Network storage 160 can also be implemented as a storage area network (SAN), which couples remote storage devices to a server (e.g., a storage server), such that the remote storage devices appear as locally-attached storage devices to the server's OS, for example. In light of the present disclosure, it will be appreciated that network storage 160 can be implemented by any type of computer-readable storage medium, including, but not limited to, internal or external hard disk drives (HDD), optical drives (e.g., CD-R, CD-RW, DVD-R, DVD-RW, and the like), flash memory drives (e.g., USB memory sticks and the like), tape drives, removable storage in a robot or standalone drive, and the like.

It will be appreciated that, in light of the present disclosure, system 100 and network 130 can include other components such as routers, firewalls and the like that are not germane to the discussion of the present disclosure and will not be discussed further herein. It will also be appreciated that other configurations are possible. For example, clients 110(1)-(N) can be directly coupled to server 120.

It is also noted that the letter N is used to indicate a variable number of devices or components. For example, a variable number of client systems are implemented in the system. Although the letter N is used in describing a variable number of instances of each of these different devices and components, a repeated use of the letter N does not necessarily indicate that each device and component has a same number of N instances implemented in the system.

Figure 2:
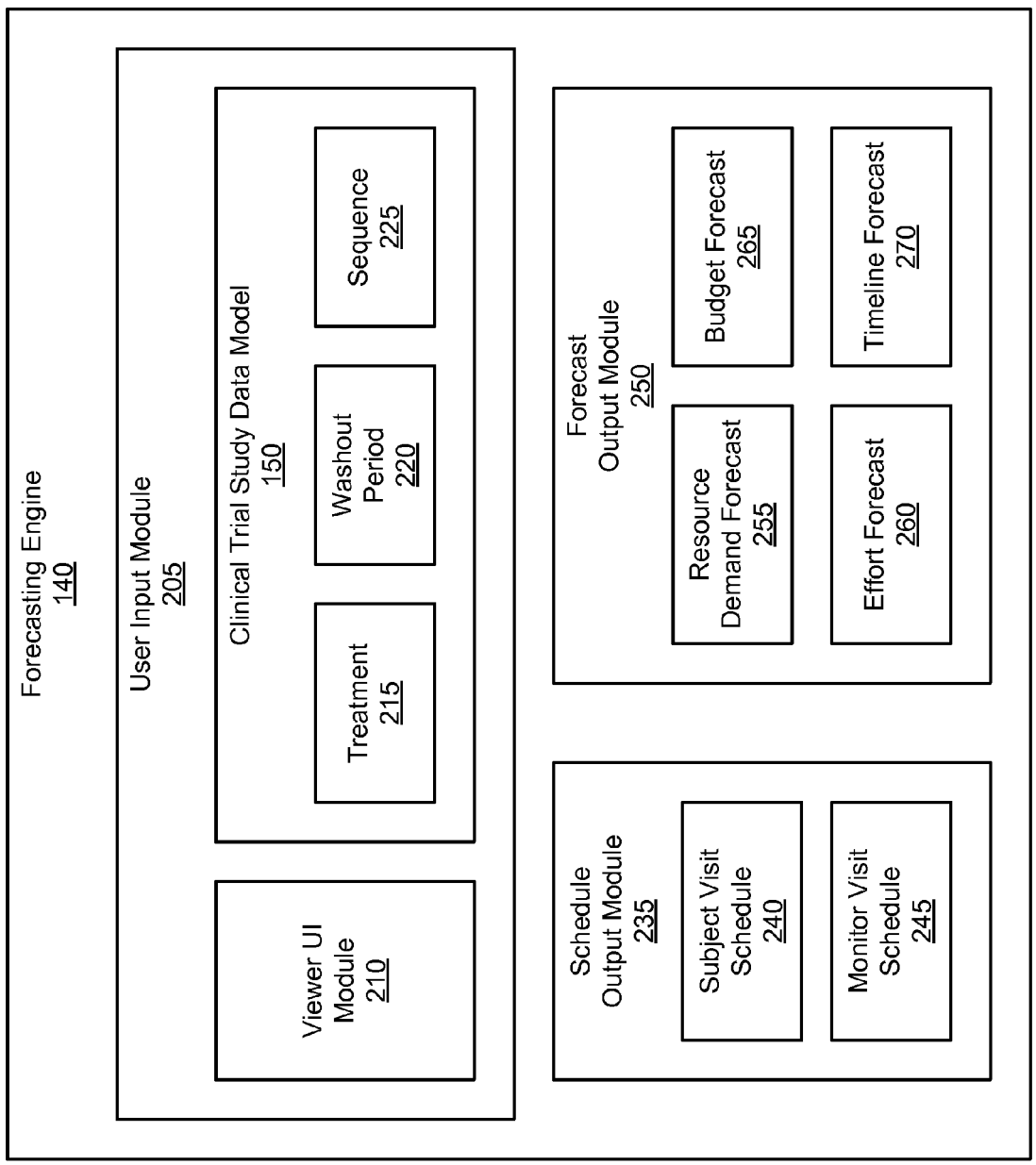
FIG. 2 is a simplified block diagram illustrating components of an example forecasting engine in which the present disclosure can be implemented, according to one embodiment.

FIG. 2 is a simplified block diagram illustrating components of an example forecasting engine 140 in which the present disclosure can be implemented. Forecasting engine 140 can be implemented on server 120, and can include various components communicatively coupled to one another, such as user input module 205, viewer user interface (UI) module 210, schedule output module 235, and forecast output module 250. Forecasting engine 140 can be triggered to execute in response to a user request (e.g., a user request received from a user interface) for generating a study (e.g., generating a data model object that represents a particular study), generating a schedule (e.g., a subject visit schedule and/or a monitor visit schedule) and/or a forecast (e.g., a resource demand, effort, cost, and/or timeline forecast) and/or upon receiving data used to complete calculations for generation of an effort, resource demand, cost and/or timeline forecast (e.g., receiving updated task information with updated unit cost and unit hours, updated resource information with updated billing rates of resources, and the like). The components of forecasting engine 140 are further discussed below.

User input module 205 includes a viewer UI module 210. Viewer UI module 210 is configured to provide user access to forecasting engine 140 by communicating with a user interface (e.g., communicating with user interface 115 on a client 110 via network 130). Viewer UI module 210 is configured to receive input data received from a user interface (e.g., user input, or data entered by a user into user interface 115 on client 110 and received at viewer UI module 210). In response to a user request (e.g., a request received by viewer UI module 210 from user interface 115) to generate a particular cross-over study, user input module 205 is configured to generate a representation of the particular cross-over study (also referred to as a data model object), using clinical trial study data model 150 as a template. Clinical trial study data model 150 defines a number of operational parameters that describe various aspects of a given cross-over study. Various operational parameters relate to treatment entity 215, washout period entity 220, and sequence entity 225 of clinical trial study data model 150. Operational parameters are further discussed below in connection with FIG. 3.

Viewer UI module is configured to transmit requests for the various operational parameters to a user interface, where a user can specify values of the operational parameters in the user interface. Viewer UI module is also configured to receive input data (from the user interface) of the specified operational parameter values that correspond to the particular cross-over study. Once the operational parameters (e.g., user input) are received from the user interface, user input module 205 is configured to populate the data model object corresponding to the particular cross-over study with the operational parameters. Viewer UI module 210 is configured to temporarily store the data model object locally (e.g., in a cache or buffer) and is also configured to communicate the data model object to network storage 160 for storage as clinical trial study data 170. Viewer UI module 210 is also configured to communicate the data model object and/or operational parameters to schedule output module 235 and forecast output module 250.

Schedule output module 235 is configured to use the data model object and/or operational parameters to generate various schedules for the particular cross-over study that is represented by the data model object, such as subject visit schedule 240 and monitor visit schedule 245, which are discussed below in connection with FIGS. 5, 6A, and 6B. Schedule output module 235 is configured to temporarily store the various schedules locally (e.g., in a cache or buffer) and to communicate the various schedules to network storage 160 for storage as part of clinical trial study data 170. The various schedules can be associated (in clinical trial study data 170) with the data model object that represents the particular cross-over study. Schedule output module 235 is also configured to communicate the various schedules to forecast output module 250. Schedule output module 235 is also configured to communicate the various schedules to viewer UI module 210 of user input module 205, where viewer UI module 210 can communicate the schedules (e.g., output data) to a user interface for display to a user.

Forecast output module 250 is configured to use the data model object, operational parameters, and/or various schedules to generate various forecasts for the particular cross-over study that is represented by the data model object, such as resource demand forecast 255, effort forecast 260, budget forecast 265, and timeline forecast 240, which are discussed below in connection with FIGS. 7-10. Forecast output module 250 is configured to temporarily store the various forecasts locally (e.g., in a cache or buffer) and to communicate the various forecasts to network storage 160 for storage as part of clinical trial study data 170. The various forecasts can be associated (in clinical trial study data 170) with the data structure that represents the particular cross-over study. Forecast output module 250 is also configured to communicate the various forecasts to viewer UI module 210 of user input module 205, where viewer UI module 210 can communicate the forecasts (e.g., output data) to a user interface for display to a user.

Figure 3:
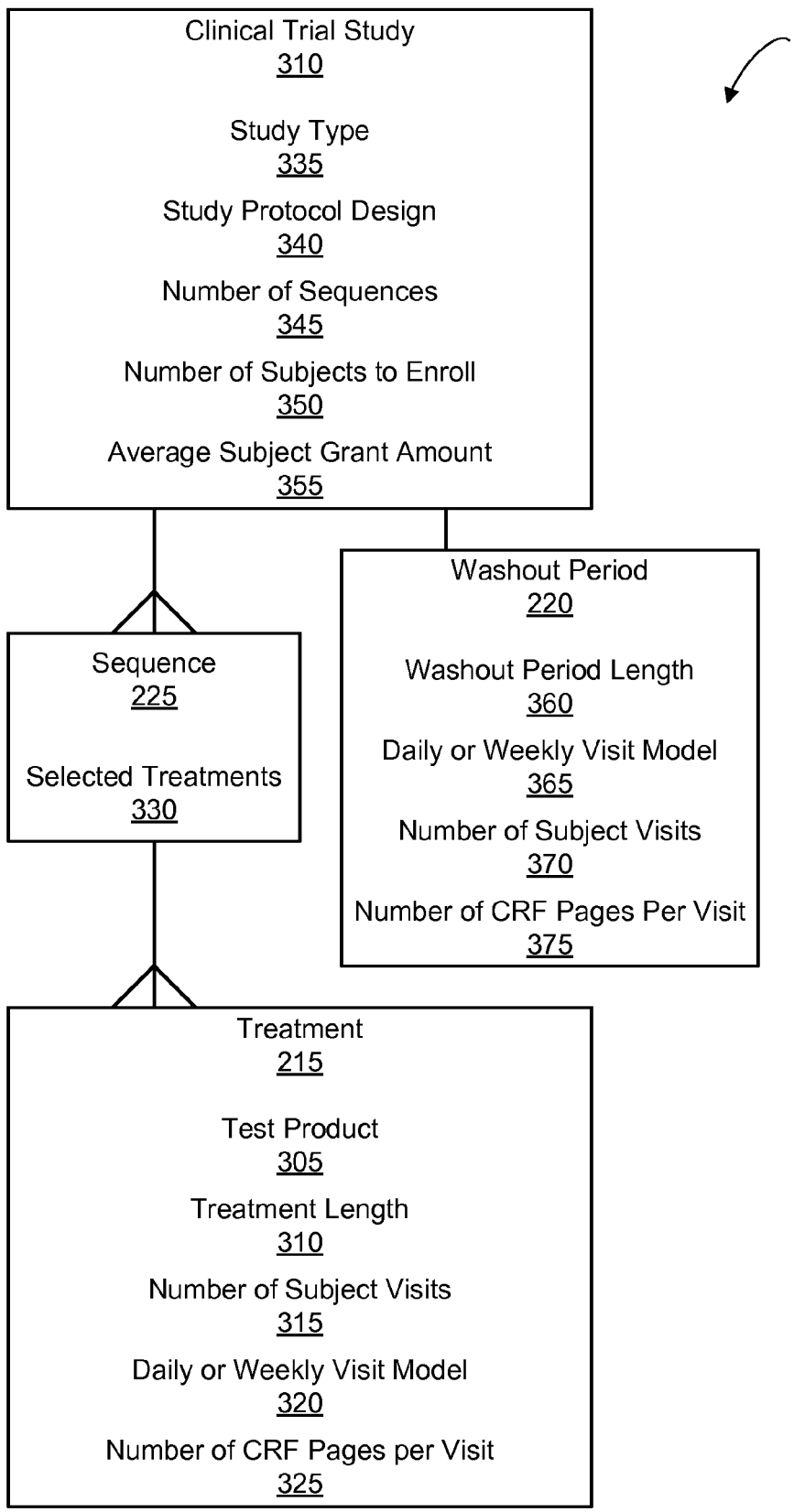
FIG. 3 is a simplified block diagram illustrating components of an example data model of a clinical trial study, according to one embodiment.

FIG. 3 is a simplified block diagram illustrating components of an example data model for a clinical trial study (depicted in FIG. 3 as a clinical trial study data model 150). Clinical trial study data model 150 (or simply data model 150) represents a clinical trial study, such as a study implementing a cross-over treatment design (also referred to as a cross-over study). Data model 150 includes a clinical trial study entity 310, a washout period entity 220, a sequence entity 225, and a treatment entity 215. Clinical trial study entity 310 has a one-to-many relationship with sequence entity 225, which in turn has a one-to-many relationship with treatment entity 215. Thus, a data model object can be generated from data model 150 that represents a particular study, where the data model object can include a number of instances of sequence entity 225 (also referred to as sequences), which in turn includes a number of instances of treatment entity 215 (also referred to as treatments) and a number of instances of washout period entity 220 (also referred to as washout periods). In other words, a data model object that represents a cross-over study includes a collection of sequences, where a sequence includes a collection of treatments and intervening washout periods.

While clinical trial study entity 310 is illustrated as having a one-to-one relationship with washout period entity 220 (indicating the same washout period is used in each instance of sequence entity 225 associated with a particular instance of clinical trial study entity 310), washout period entity 220 can alternatively have a one-to-one relationship (not shown) with sequence entity 225 (indicating that a different washout period can be used in each instance of sequence entity 225 associated with a particular instance of clinical trial study entity 310). As can be seen, data model 150 includes a number of operational parameters, which define how the study is modeled and implemented, as further discussed below.

Treatment entity 215 includes a number of operational parameters, such as test product 305, treatment length 310, number of subject visits 315, daily or weekly visit model 320, and number of case report form (CRF) pages 325. Test product 305 is a medicinal drug or medical device being tested during a test treatment, where test product 305 is administered to (or used with) a number of subjects during the test treatment. One or more test products 305 may be tested in various test treatments during the cross-over study. Test product 305 may also include a specified drug dosage or amount of device usage, where the same test product 305 can be tested with different dosages or usage in two or more test treatments. Test product 305 can be selected from a number of possible test products (e.g., a list of test products can be displayed in user interface 115 for user selection) or can be entered by the user. Treatment length 310 is the time duration during which test product 305 is tested (e.g., time during which a subject receives the medicinal drug or uses the medical device), which can be specified in days, weeks, or months.

Number of subject visits 315 is the number of times that a subject will meet or visit with the investigator at an investigator site to be medically examined. An investigator site is a location (e.g., doctor's office or medical offices) to which each subject goes to receive the test product or to be medically examined to record data about the subject (and in some studies, subjects stay overnight during the study). Daily or weekly visit model 320 indicates whether the subject visits occur daily or weekly (e.g., indicates whether the user-specified value of treatment length 310 should be interpreted as days or weeks, where the subject visits can be distributed over the treatment length). Number of case report form (CRF) pages per visit 325 is the number of CRF pages that will be generated at each subject visit during the treatment. A case report form includes a number of CRF pages that record CRF data. A case report form is used by the investigator (e.g., medical staff, such as employees, nurses, doctors, and the like) to record (raw) data about a subject that is specific to the clinical trial study, such as a subject's vital signs (e.g., heart rate, blood pressure, blood tests, and the like) that are also recorded in the subject's medical chart filled out by medical staff. A case report form also records any observed effects on the subject (e.g., whether the subject's condition is improving or worsening while using test product 305). A case report form can also include other information about the subject, such as a unique identifier of the subject (e.g., an investigator-assigned number).

At least one treatment (e.g., set as a default treatment) is a control treatment, during which the subject receives a placebo or otherwise does not receive or use test product 305. Since studies are often double-blind (indicating that the investigator and the subject do not know whether the subject is receiving the test product or a placebo), the CRF pages may indicate the sequence being received by the subject, but will not indicate whether the test treatment or control treatment is being received by the subject.

Washout period entity 220 includes information regarding a given washout period, such as a washout period length 360, a daily or weekly model 365, a number of subject visits 370 (optional), and a number of CRF pages per visit 375 (optional). Washout period length 360 is a length of time between treatments, and daily or weekly model 365 indicates whether the length is expressed in days or weeks. Washout period length 360 should be long enough for the subject to return to a control state (e.g., long enough to flush out the drug taken during a treatment before starting the next treatment, or let the effects of using the medical device wear off before starting the next treatment). A common value of washout period length 360 is twice the half-life of the medicinal drug being tested. Washout period length 360 is used to avoid cross-drug interaction or residual carryover effects sullying the result data of the study. Number of subject visits 370 can optionally be included, where the subject is medically examined at each visit during the washout period without receiving a treatment. Number of CRF pages per visit 375 can also (optionally) be included, where a number of CRF pages are generated at each (optional) subject visit during the washout period.

Sequence entity 225 can optionally include a number of selected treatments 330, or the number of treatments to be included in a given sequence. A number of sequences can be automatically generated or built to include a randomized collection of treatments that meets the number of selected treatments 330, using a study design 340 (as further discussed below). A number of sequences can also be manually generated or built by the user to include a user-selected collection of treatments that meets the number of selected treatments 330. A user builds a sequence by selecting a number of treatments (and washout period) to be included in the sequence. The user can combine the treatments (where a washout period intervenes between two treatments, resulting in an alternating combination of treatments and washout periods) in any particular order in a sequence, where the combination is built according to the study protocol design for the clinical trial study (e.g., a user can manually build a sequence according to a study protocol design 340).

Clinical trial study entity 310 also includes a number of operational parameters, such as study type 335, study design 340, number of sequences 345, number of patients to enroll 350, and average subject grant amount 355. Study type 335 is the type of study on which clinical trial study 310 is modeled (e.g., cross-over study type, traditional study type). While other study types can be supported and selected, the present disclosure herein refers to a study type of cross-over study type being selected by the user.

Study protocol design 340 is the study protocol design used to generate or build sequences (e.g., automatic sequence generation and/or manual sequence generation). A number of pre-configured study designs 340 that define automatic sequence generation can be supported. While other study designs can be supported and selected, the present disclosure herein refers to cross-over study designs, examples of which include Balaam's Design and Latin Square, among other designs.

Figure 4:
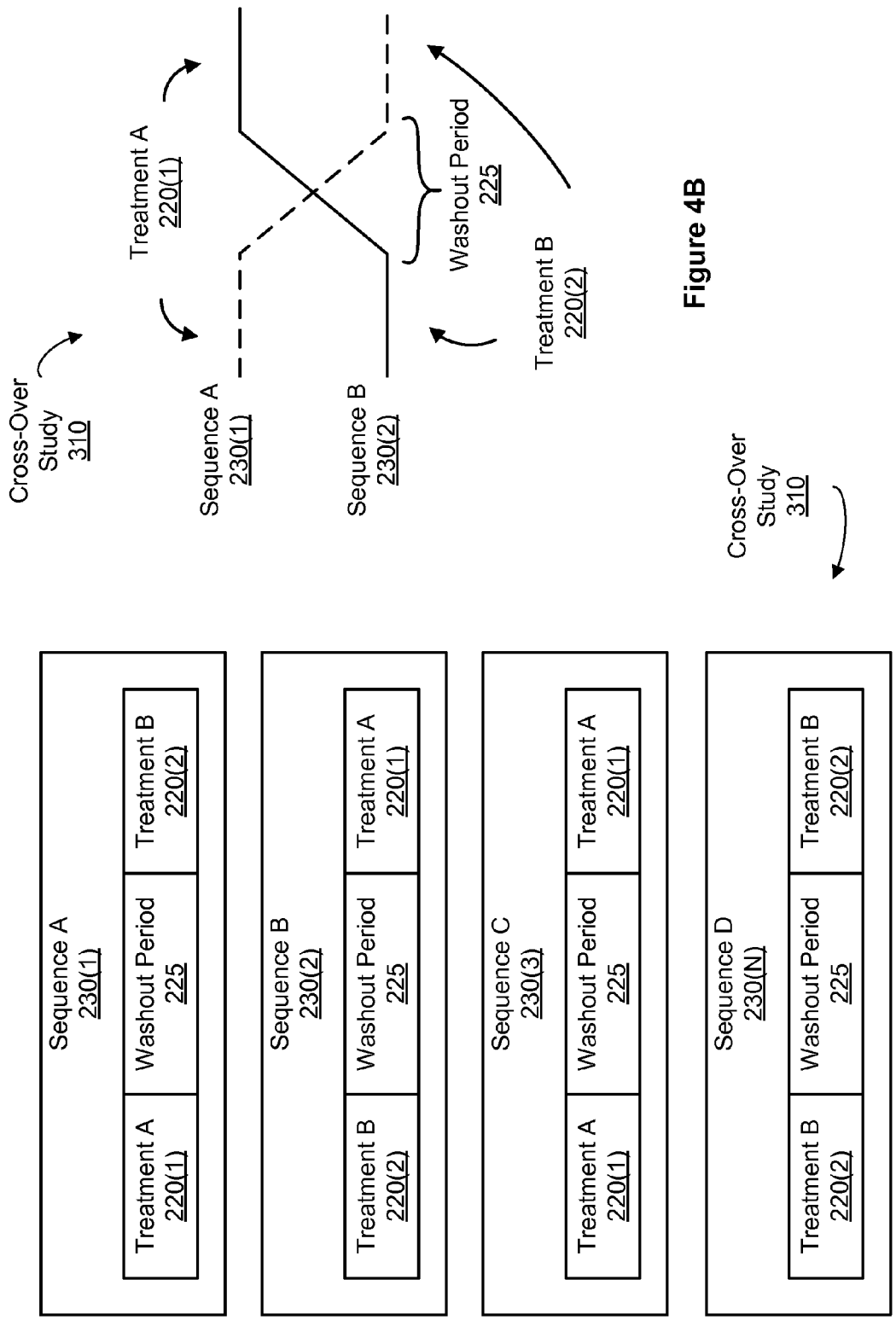
FIGS. 4A and 4B are simplified block diagrams illustrating components of an example clinical trial study, according to one embodiment.

Balaam's Design applies to a two treatment cross-over study, and is often used to investigate carry over effects by repeating a given treatment in a sequence, without crossing over to the other treatment. As illustrated in the cross-over study of FIG. 4A, Balaam's Design generates four sequences (sequences A through D) from two treatments (treatments A and B). Sequence A 230(1) includes treatment A 220(1), washout period 225, and treatment B 220(2). Sequence B 230(2) includes treatment B 220(2), washout period 225, and treatment A 220(1). Sequence C 230(3) includes treatment A 220(1), washout period 225, and treatment A 220(1). Sequence D 230(4) includes treatment B 220(2), washout period 225, and treatment B 220(2).

The Latin Square design produces an N by N array of number N treatments 220, with each treatment 220 occurring once in each row and once in each column. The rows (or alternatively, the columns) of the N by N array are the generated sequences 230. As illustrated in the cross-over study of FIG. 4B, Latin Square generates two sequences (sequences A and B) from two treatments (treatments A and B). Sequence A 230(1) is illustrated using a broken line, and includes treatment A 220(1), washout period 225, and treatment B 220(2). Sequence B 230(2) is illustrated using a solid line, and includes treatment B 220(2), washout period 225, and treatment A 220(1).

Returning to FIG. 3, number of sequences 345 is a particular number of sequences selected from the generated sequences, which can include "all" or all sequences generated. As the number of treatments grows, the number of generated sequences often grows much more quickly (such as in Latin Square). Rather than use every sequence generated by a study design (which can be too many sequences to be tested in a reasonable amount of time), a user can request a particular number of sequences to be used in the clinical trial study, which are then randomly selected from the generated sequences.

Number of subjects to enroll 350 is the total number of subjects that are needed to enroll in (or volunteer to participate in) the clinical trial study to undergo randomized treatment. The subjects that enroll in the clinical trial study will each randomly receive one of the sequences used during the study (e.g., the subjects are randomly divided into subject groups, with each group randomly assigned to a particular sequence of the study). Average subject grant amount 355 is the average amount of money that is paid to the investigator for each subject. Average subject grant amount 355 includes the cost of the investigator to run the clinical study trial. An actual subject grant amount can vary depending on whether the subject completes the study (e.g., the investigator would receive 100% of the grant amount for a completed subject, compared to 75% of the grant amount for a dropped subject).

Other operational parameters of clinical trial study entity 310 (which are not illustrated in FIG. 3) that can be specified by the user include cost per bednight for a subject, such as in a Phase I trial, where subjects stay at the investigator site for the duration of the study. Cost per bednight can include the cost of providing room and board, meals, staff, and other similar services for a subject during a given night of a study. Other operational parameters can also include the number of investigator sites and the country in which each site is located (where each subject group can be assigned to one of the investigator sites, with a number of subject groups visiting each investigator site), number of subjects that need to be randomized or enrolled in each country, average grant amount per subject of each country, billing rates of resources (e.g., employees of the investigator or outsourced labor), estimated cost of labor and travel (e.g., for outsourced labor), CRF monitoring rate (e.g., the number of CRF pages that can be monitored, or collected and verified, within a given time period), time required for data entry of CRF pages, estimated number of queries per 100 CRF pages, baseline visit monitoring time required to collect pages, an enrollment period that includes start and end dates, an estimated subject enrollment rate, a screening failure rate (e.g., an estimated number of subjects expected to fail the screening process required to participate in the study), a subject drop rate (e.g., an estimated number of subjects expected to drop out of the study), a study start date (e.g., the date that the study is expected to begin, defined as the date that the sponsor starts identifying investigator sites and billable activity is begun), a study end date (e.g., the date by which the study is expected to be complete, defined as the date that all activity stops, such as the date that the final report is finalized), total study duration (e.g., the estimated study duration, defined as the study end date minus the study start date), duration of treatment phase (e.g., the estimated treatment phase duration), and the like. These other operational parameters are also used in generating various schedules and forecasts, as further discussed below.

Figure 5:
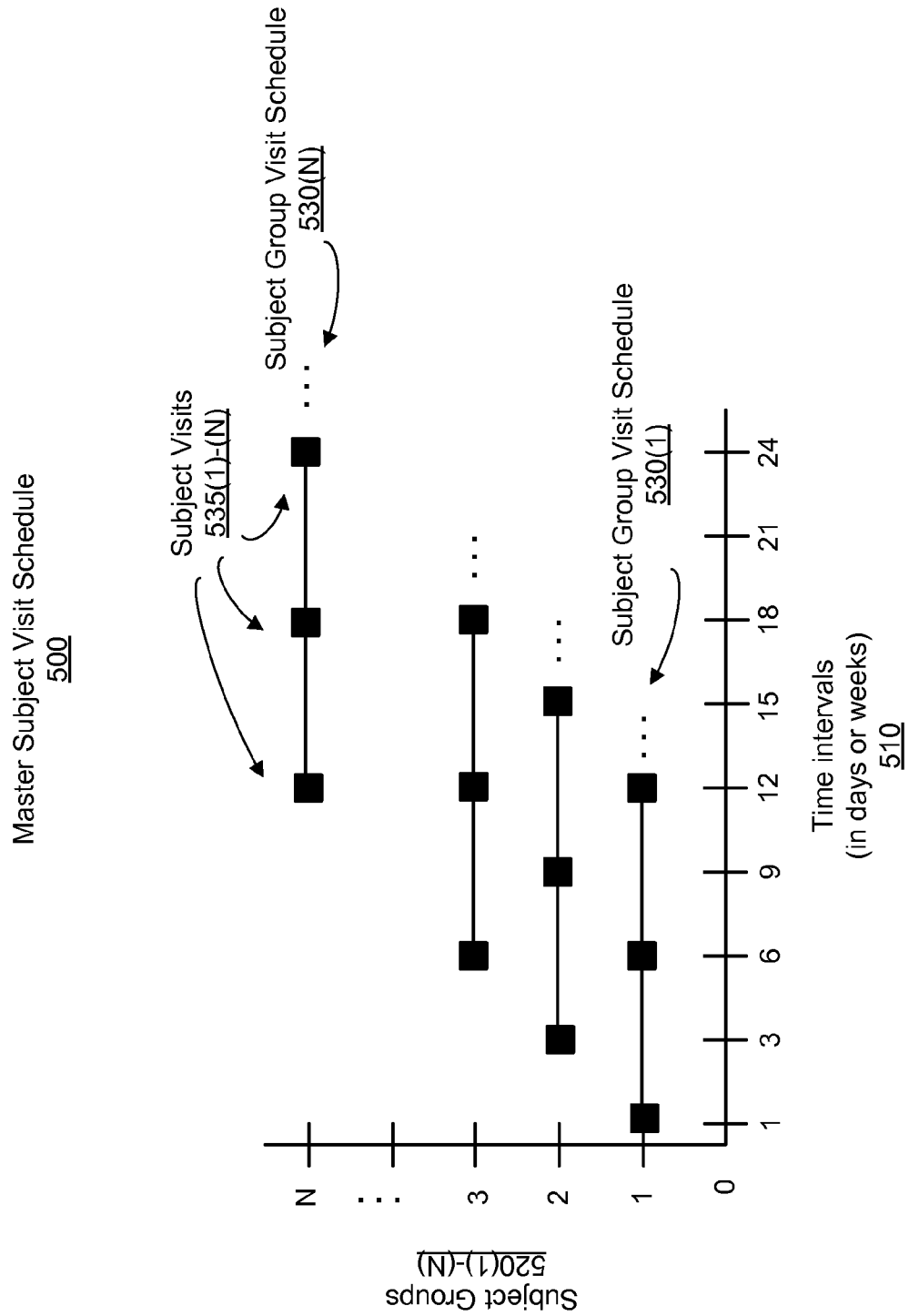
FIG. 5 is a simplified graphical representation illustrating elements of an example subject visit schedule, according to one embodiment.

FIG. 5 is a simplified graphical representation illustrating elements of an example subject visit schedule 500. Once the operational parameters of a particular study are known (e.g., user-specified values are received), the operational parameters can be provided to schedule output module 235 (e.g., the operational parameters are provided individually to schedule output module 235 and/or are provided as part of the data model object that represents the particular study) and are used to generate subject visit schedule 240. In one embodiment, schedule output module 235 establishes a subject group for each sequence that is included in the clinical trial study, where the number of subject groups is equal to the number of sequences 345. It is noted that the sequences included in the clinical trial study (as indicated by number of sequences 345) may be fewer than the total number of possible sequences that are generated using study design 340. In one embodiment, schedule output module 235 also uses number of subjects to enroll 350 to divide the subjects among the subject groups (where the subjects will be randomized to the subject groups). In one embodiment, each subject group is assigned a number of subjects equal to number of subjects 350 divided by number of sequences 345 (also referred to as the number of subjects per subject group).

Since each subject group is assigned to (or associated with) a particular sequence, the subjects assigned to a given subject group will receive the treatments of the sequence associated with the given subject group. For each sequence, treatment length 310, number of subject visits 315, and daily or weekly visit model 320 of each treatment included in the given sequence can be used to determine a subject visit schedule for each subject group, also referred to as a subject group visit schedule 530. FIG. 5 illustrates a number of subject group visit schedules 530(1)-(N) for a number of subject groups 520(1)-(N). A subject group visit schedule indicates the total number of subject visits required of each subject in the given subject group during the study. For example, a subject group visit schedule can be generated for a subject group that is associated with sequence A that includes treatment A having a treatment length of 6 weeks with 6 visits (e.g., treatment length 310 of 6, number of subject visits 315 of 6, and a weekly visit model 320), a washout period of 2 weeks (e.g., washout period length 360 of 2 with weekly model 365, without requiring any additional visits during the washout period), and treatment B having a treatment length of 8 weeks with 16 visits (e.g., treatment length 310 of 8, number of subject visits 315 of 16, and a weekly visit model 320). Thus, for this particular sequence A, the subject group visit schedule indicates a total of at least 24 subject visits required of the subject group over a 16 week schedule.

Subjects can also begin the testing or treatment phase on a staggered basis, in order to avoid overwhelming the available resources of the investigator site (e.g., not enough staff available to treat the subjects). As illustrated in FIG. 5, subjects of subject group 520(1) begin treatment on the first day of week 1 and subjects of subject group 520(2) begin treatment later on the first day of week 3 (as indicated by the darkened squares indicating subject visits 535 placed on weeks 1 and 3 of time intervals 510 (in weeks). FIG. 5 illustrates a master subject visit schedule 500, which indicates the subject group visit schedules 530 for all subject groups 520, and thus indicates the visit schedules of all subjects enrolled in the particular study. In one embodiment, subjects of a particular subject group need not begin treatment at the same time, but instead can begin treatment at one of a number of available visits (e.g., the initial subject visits illustrated by darkened squares on time intervals 1, 3, 6, and so on). Such subjects would still follow the subject visit schedule associated with the subject's assigned subject group, although at an offset (e.g., earlier or delayed, as compared with the original subject group visit schedule).

Once a subject group visit schedule has been generated for each subject group, subject group visit schedule 530 indicates the estimated length of time for each subject group 520 to complete the testing phase (e.g., 16 weeks in the above example). Master subject visit schedule 500 indicates a total estimated length of time for full completion of the testing phase (e.g., a total amount of time for all staggered subject group visit schedules 530(1)-(N) to be completed). Master subject visit schedule 500 can include subject groups for a single investigator site or for multiple investigator sites. Schedule output module 235 can communicate a visual representation of master subject visit schedule 500 to viewer UI module 210, which in turn communicates the visual representation to a user interface 115 for display to a user. Schedule output module 235 can store master subject visit schedule 500 in network storage 160 as clinical trial study data 170, where master subject visit schedule 500 is associated (in clinical trial study data 170) with the data model object that represents the particular study.

FIG. 6A is a simplified graphical representation illustrating elements of an example data flow 600 that can be generated by schedule output module 235. Schedule output module 235 is configured to use master subject visit schedule 500 to calculate an estimated data flow of the testing phase. For each subject visit during treatment, data about each subject is recorded in a number of case report form (CRF) pages 620 (also referred to as subject data or CRF data), as specified by the data model. In implementation of the study, the number of CRF pages can be greater than (e.g., a negative reaction to the treatment may require additional CRF pages to record additional information about the subject) or less than the estimated number of CRF pages (e.g., a subject drops out of the study and subsequent CRF pages are not recorded).

Schedule output module 235 can calculate an estimated data flow of CRF pages, using the master subject visit schedule to determine when CRF pages 620 are estimated to be generated over time intervals 610 (which can be in days or weeks, as specified by the data model object). For example, an estimated total number of CRF pages (or estimated CRF page total) can be calculated for a given time interval (e.g., day or week) by multiplying the number of subject group visits scheduled for the given time interval (e.g., 5 subject group visits on day 12) by the number of CRF pages generated per subject visit (e.g., each visit generates 5 CRF pages per subject) and by the number of subjects per subject group (e.g., 25 subjects per group). In this example, a total of 625 CRF pages are generated on day 12. It is noted that the number of CRF pages generated per subject visit may be a different number for each subject group visit, depending on the number of CRF pages per visit defined for the treatment or washout period associated with the subject group visit.

The estimated data flow is represented in FIG. 6A as a line curve of cumulative data flow for a single investigator site, or summation of estimated CRF page totals for the time intervals of the testing phase. Other representations of the data flow of CRF pages can also be determined (e.g., total estimated data flow for all investigator sites, individual estimated CRF page totals generated per time interval for one or more investigator sites, and the like). Schedule output module 235 can communicate a visual representation of estimated data flow to viewer UI module 210, which in turn communicates the visual representation to a user interface 115 for display to a user. Schedule output module 235 can store the estimated data flow in network storage 160 as clinical trial study data 170, where the estimated data flow is associated (in clinical trial study data 170) with the data model object that represents the particular study.

The estimated data flow can also be used to determine a monitor visit schedule. Rather than perform collection and verification of CRF data at the end of the study, a monitor is responsible for performing monitoring periodically throughout the study. For example, the monitor can visit a number of investigator sites periodically to perform CRF data collection and verification. Depending on the location of the investigator site, a monitor may be able to easily travel to a local site or may require travel to visit the remote site. Also, the monitor may complete collection and verification within a few hours on a given day or within a few days (which may also require a hotel stay, if at a remote site), depending on the amount of CRF data to monitor. Since the cost of a monitor can be quite expensive, schedule output module 235 is also configured to determine an optimal monitoring schedule that minimizes labor and travel costs from the estimated data flow, rather than using a default schedule of one monitor visit every number of time intervals (e.g., once every week).

In some embodiments, it is preferable to schedule a monitor to visit as often as is necessary to collect available CRF data, without requiring the monitor's visit to last for several days as the monitor performs the collection and verification of CRF data. In some embodiments, it is also preferable to schedule monitor visits to maximize the collection and verification of CRF data during a given visit. For example, a monitor can be scheduled to perform monitoring using a default schedule, such as every week. Such default monitoring would result in inefficient use of the monitor's time, such as a short visit (e.g., a two hour visit) if the data flow is low for that particular week, or a long visit (e.g., multiple days) if the data flow is high for that particular week. One way to improve efficiency is to schedule the monitor visit at a time when the data flow reaches a minimum threshold amount of CRF data. Thus, the monitor would not need to be scheduled for multiple short visits if the CRF data of those visits can be collected and verified in a single longer visit. Such an improvement could minimize the number of monitor visits, which would also minimize any travel expenses involved for each short visit.

In some embodiments, it is also preferable to schedule monitor visits before CRF data flow reaches a maximum threshold amount of CRF data, in order to avoid lengthening a monitor visit to collect and verify a large amount of CRF data. If a large amount of CRF data can be collected and verified in multiple shorter visits (e.g., single day visits), the monitor would not need to be scheduled for a long visit (e.g., multiple days, which would likely include hotel stays and other travel costs). Such an improvement could minimize travel costs, such as hotel stays. Another way to improve efficiency is to schedule multiple monitors per visit, in order to reduce the number of visits without reducing the amount of CRF data collected and verified. Other efficiencies can also be implemented.

Schedule output module 235 can analyze the CRF data flow to schedule the monitor visits as needed. In one embodiment, schedule output module 235 is configured to schedule monitor visits within a window of time that begins once the estimated data flow reaches a minimum threshold amount of CRF data flow and that ends once the estimated data flow reaches a maximum threshold amount of CRF data flow. Such minimum and maximum threshold amounts of CRF data flow (e.g., number of CRF pages) can be specified by the user as operational parameters of the data model. FIG. 6B illustrates a simplified graphical representation illustrating elements of an example master monitor visit schedule 650, which can include one or more monitor visit schedules (e.g., schedules of candidate monitors that are used in hiring a candidate monitors, or various schedules of a single monitor that are used in identifying a cost-efficient monitor visit schedule).

In another embodiment, schedule output module 235 can use a CRF monitoring rate to identify a target amount of available CRF data flow to be processed during a monitor visit (where the monitor visit may have a length of hours or days, for example) and to schedule the corresponding monitor visit. A CRF monitoring rate is an estimated number of CRF pages that can be collected and verified within a time period by a monitor. A CRF monitoring rate can be estimated by the user as part of the operational parameters of the data model, can be estimated and provided by a candidate monitor to the investigator as part of the operational parameters of the data model for use in hiring the candidate monitor, or can be estimated from historical data of previous monitoring performed by the candidate monitor.

For example, if a monitor has a CRF monitoring rate of 2000 CRF pages per eight hour visit, schedule output module 235 can determine a target amount of available CRF pages from the CRF monitoring rate, which in this example would be 2000 CRF pages for a single eight hour visit (e.g., a daily visit to minimize travel costs). Schedule output module 235 can also determine that a monitor visit 630 (illustrated as solid circles) should be scheduled when 2000 CRF pages (or close to 2000 CRF pages) are available for the monitor to process. A minimum and maximum threshold amount of CRF pages can also be used in such an embodiment, where the minimum threshold amount can be defined as a particular amount less than the target amount of available CRF pages (e.g., 1800 CRF pages, or 2000 CRF pages minus 200 CRF pages) and the maximum threshold amount can be defined as a particular amount greater than the target amount of available CRF pages (e.g., 2200 CRF pages, or 2000 CRF pages 200 CRF pages). In such an embodiment, a monitor visit can be scheduled during a window of a time that begins once the estimated data flow reaches the minimum threshold amount of CRF data flow and that ends once the maximum threshold amount of CRF data flow. Monitor visits 630(1)-(N) are also illustrated in FIG. 6B as part of monitor visit schedule 680(N).

Schedule output module 235 can also determine another monitor visit schedule based on different visit lengths. For example, if monitor visits 630(1)-(N) involved hotel stays and other associated travel costs (e.g., the visit length was multiple days long, as determined from the CRF monitoring rate), schedule output module 235 can generate a monitor visit schedule using smaller visit lengths (e.g., an eight hour or daily visit), which can minimize associated travel costs. Thus, a monitor would process fewer CRF pages during each visit, requiring additional monitor visits to be scheduled, such as monitor visits 640 (illustrated as solid squares). Schedule output module 235 can compare one or more monitor visit schedules and their associated costs to determine whether a particular monitor visit schedule is beneficial, such as by comparing any travel cost savings or increases with any labor cost savings or increases. Monitor visits 640(1)-(N) are also illustrated in FIG. 6B as part of monitor visit schedule 680(1).

Additionally, a monitor can also be selected from a pool of different monitors to perform monitoring duties. For example, a first monitor may be able to perform collection and verification of CRF pages at a particular CRF monitoring rate (e.g., 1200 CRF pages per eight hour visit), resulting in a first monitor visit schedule 680(1). A second monitor may have a more efficient monitoring rate (e.g., 2000 CRF pages per eight hour visit), resulting in a second monitor visit schedule 680(N). While the second monitor visit schedule includes fewer monitor visits (and a smaller amount of labor costs), the second monitor visit schedule may also have higher associated costs, such as travel and hotel costs due to the second monitor being located remotely from the site. Thus, the first monitor and first monitor visit schedule may be chosen for the study.

Schedule output module 235 can communicate a visual representation of master monitor visit schedule 650 to viewer UI module 210, which in turn communicates the visual representation to a user interface 115 for display to a user. Schedule output module 235 can store master monitor visit schedule 650 in network storage 160 as clinical trial study data 170, where master monitor visit schedule 650 is associated (in clinical trial study data 170) with the data model object that represents the particular study.

FIG. 7 is a simplified block diagram illustrating elements of an example resource demand forecast generated by forecast output module 250. A resource is an employee of the investigator or outsourced labor (e.g., a monitor) that performs one or more tasks to implement a clinical trial study, and a resource demand forecast is a summary of the resources and associated costs that are needed to implement the clinical trial study. Resource information about available resources can be received as part of the operational parameters specified by a user and/or can be specified a system administrator during a separate process. Resource information can be stored in network storage 160 as part of clinical trial study data 170. Resource information can include a number of operational parameters that are defined as part of the data model, such as a description of each resource (e.g., employee title), a billing rate of each resource (e.g., hourly billing rate), a department of each resource, any additional costs associated with each resource (e.g., an estimated travel cost or cost of using a particular facility or piece of equipment), and one or more tasks performed by each resource. Resource information can be updated by a user and/or a system administrator, where such updated resource information is provided via a user interface to reflect updated resource information (e.g., a new billing rate for a resource). A user and/or system administrator can also define a new resource and associated resource information, which is added to resource information.

A task is an activity that is performed in implementing the study. Each resource can be assigned one or more tasks to perform. For example, during the setup phase of the study, a database needs to be designed to store the result data collected during the testing phase of the study. A resource, such as a program analyst, can be assigned to perform the task of designing a database. Similarly, during the analysis phase of the study, a draft report that describes the findings of the study needs to be written. A resource, such as a medical writer, can be assigned to perform the task of writing the draft report. A system administrator can define a resource to be automatically (e.g., without user intervention) associated with one or more tasks (where such automatic associations are stored in resource information) or a user and/or a system administrator can assign and re-assign (e.g., remove an automatic association and manually create a new association) a resource to perform a task. A task can be assigned to an investigator employee or can be outsourced to a service provider (e.g., a monitoring firm that is responsible for sending monitors to the investigator site to collect and verify CRF data).

Resources and tasks can be selected by a user to be associated with the study, indicating that the selected resources and tasks are needed to implement the study. A list of known tasks and a list of known resources can be stored in network storage, where certain tasks can be selected by a user in a user interface (e.g., from a drop down menu) and assigned to certain resources. A subset of the known tasks can also be automatically associated (e.g., without user interaction) with the study, in response to an existing association between the subset of tasks with a resource that is selected by the user (e.g., selected in a user interface, such as from a drop down menu). In such an embodiment, user selection of a certain resource will automatically associate the subset of tasks (which are associated with the certain resource) with the study. The resources and tasks associated with the study can be displayed in various forecasts. Costs and time estimations (e.g., unit cost and unit hours) associated with each resource and/or task can also be displayed in the various forecasts.

A resource demand forecast 255 is illustrated in FIG. 7. Resource demand forecast 255 includes a list of resources 700 needed to implement a study, each of which includes a subset list of tasks 705 that the resource 700 is responsible for performing. For example, a first entry 700(1) in resource demand forecast 255 indicates that a monitor resource is needed to implement the study, where the monitor is assigned tasks 705(1), traveling to investigator sites, and 705(2), collecting and verifying CRF data. Resource demand forecast 255 also includes a unit of measure 710, a number of units 715, unit hours 720, unit cost 725, extended unit hours 730, and extended unit cost 735, which are associated with each resource 700.

Unit of measure 710 is the particular work product of the resource. In other words, the resource produces or implements the unit of measure as a result of completing the task(s). Number of units 715 is the estimated number of instances of the work product needed. For example, a monitor will complete the assigned tasks to produce a monitor visit, where the monitor will perform the tasks to produce or implement 100 monitor visits. Unit hours 720 is the estimated number of hours needed to produce a single unit or instance of the work product. Unit cost 725 is the estimated amount of money (e.g., in dollars) needed to produce or implement a single unit or instance of the work product. Unit cost 725 can include direct costs, such as an estimated resource labor cost to implement the single unit or instance of the work product, based on the resource's billing rate, and indirect costs or pass-through costs, such as facility or equipment fees and travel costs. A unit of measure is associated with a given resource (e.g., associated by a system administrator) and is stored in network storage. At least one unit hours and unit cost value pair are associated with each known task (e.g., each value pair is associated with a task by a system administrator) and are also stored in network storage. A user can also override the stored values of unit of measure, unit hours, and unit cost by specifying new values with the operating parameters.

Extended unit hours 730 is the estimated number of hours needed to produce the number of units. Extended unit hours 730 can be calculated by multiplying number of units 715 by unit hours 720. Extended unit cost 735 is the estimated amount of money needed to produce or implement the unit(s) or instance(s) of the work product. Extended unit cost 735 can be calculated by multiplying number of unit 715 by unit cost 725. Extended unit hours 730 and extended unit cost 735 can be displayed with one or more decimals (as illustrated in FIG. 7) or rounded to the nearest integer (illustrated as extended unit hours 830 and extended unit cost 835 in FIG. 8).

Forecast output module 250 can communicate a visual representation of resource demand forecast 255 to viewer UI module 210, which in turn communicates the visual representation to a user interface 115 for display to a user. Forecast output module 250 can store resource demand forecast 255 in network storage 160 as clinical trial study data 170, where resource demand forecast 255 is associated (in clinical trial study data 170) with the data model object that represents the particular study.

FIG. 8 is a simplified block diagram illustrating elements of an example effort forecast generated by forecast output module 250. Effort forecast 260 is a summary of the effort needed to implement the clinical trial study (which is expressed as the amount of time needed to implement each task of the study). Effort forecast 260 includes a list of tasks 805 that need to be performed to implement the study. Each task 805 is associated with a unit of measure 810, a number of units 815, unit hours 820, a unit cost 825, extended unit hours 830, and extended unit cost 835.

Unit of measure 810 is the particular work product of the resource. In other words, the resource produces or implements the unit of measure as a result of completing the task(s). Number of units 815 is the estimated number of instances of the work product needed. For example, task 802(1) is to initiate the study or project, where performance of the task (by a resource) will produce or implement a project initiation. Each task 805 can also include other sub-tasks that are not shown (e.g., project initiation can include assigning an initial resource to the study as a contact person, entering initial information about the study into a database, and initiating negotiation with one or more investigators to lay out how the study will be implemented). Unit hours 820 is the estimated number of hours needed to produce a single unit or instance of the work product. Unit cost 825 is the estimated amount of money (e.g., in dollars) needed to produce or implement a single unit or instance of the work product. Unit cost 825 can include direct costs, such as an estimated resource labor cost to implement the single unit or instance of the work product, based on the resource's billing rate, and indirect costs or pass-through costs, such as facility or equipment fees and travel costs. A unit of measure is associated with a given resource (e.g., associated by a system administrator) and is stored in network storage. At least one unit hours and unit cost value pair are associated with each known task (e.g., each value pair is associated with a task by a system administrator) and are also stored in network storage. A user can also override the stored values of unit of measure, unit hours, and unit cost by specifying new values with the operating parameters.

Extended unit hours 830 is the estimated number of hours needed to produce the number of units. Extended unit hours 830 can be calculated by multiplying number of units 815 by unit hours 820. Extended unit cost 835 is the estimated amount of money needed to produce or implement the unit(s) or instance(s) of the work product. Extended unit cost 835 can be calculated by multiplying number of unit 815 by unit cost 825.

Forecast output module 250 can communicate a visual representation of effort forecast 260 to viewer UI module 210, which in turn communicates the visual representation to a user interface 115 for display to a user. Forecast output module 250 can store effort forecast 260 in network storage 160 as clinical trial study data 170, where effort forecast 260 is associated (in clinical trial study data 170) with the data model object that represents the particular study.

FIG. 9 is a simplified block diagram illustrating elements of an example budget forecast generated by forecast output module 250. Budget forecast 265 is a summary of the costs incurred to implement the clinical trial study. Budget forecast 265 includes a list of tasks 905 (e.g., a list of tasks pulled from the effort forecast), where the estimated cost incurred for performing each task is displayed in a periodic total (e.g., a weekly or monthly periodic total). In the embodiment shown, an estimated cost incurred for each task is displayed in a task monthly total 915 for a number of months. Study monthly total 920 is also displayed for each month, which indicates the total estimated amount of money incurred by tasks 905 performed during a particular month (or other period of time) of the study. Task total 925 is also displayed for each task 905, indicating the total estimated amount of money incurred by the task during the entire study.

Forecast output module 250 is also configured to provide budget forecasts at various levels. For example, a high-level budget forecast can provide a single summary cost of the entire study (e.g., the study will cost an estimated $12 million dollars or $30 million dollars to implement). Low-level budget forecasts can include more granularity by displaying additional details in the summary of costs to implement the study. For example, the budget forecast can indicate the various phases of the study will each cost an estimated amount of money, or can break down the costs of each phase into various tasks that are implemented during the study (as illustrated in FIG. 9). Thus, the sponsor or user can use the budget forecast to anticipate costs of implementing the study and make decisions about how the study will be implemented. For example, the budget forecast can be used to begin negotiations with an investigator to implement the study, where budget forecast can be used to highlight where assumptions of the sponsor and investigator differ (e.g., the investigator and sponsor might have different ideas of the cost needed to implement a particular phase of the study).

Forecast output module 250 can communicate a visual representation of budget forecast 265 to viewer UI module 210, which in turn communicates the visual representation to a user interface 115 for display to a user. Forecast output module 250 can store budget forecast 265 in network storage 160 as clinical trial study data 170, where budget forecast 265 is associated (in clinical trial study data 170) with the data model object that represents the particular study.

FIG. 10 is a simplified block diagram illustrating elements of an example timeline forecast generated by forecast output module 250. Timeline forecast 270 is a summary of various initiation and completion dates of particular (e.g., important) tasks during the study. Timeline forecast 270 includes a list of milestones 1005 that are each associated with a corresponding date 1010. A milestone 1005 is a particular occurrence of a task that acts as a reference point for a timeline along which the study is estimated to be completed. Milestone 1005 can be an initiation date (e.g., start date) or a completion date (e.g., end date) of a task, with a corresponding expected date 1010 (e.g., a date including a day, month, and year). Timeline forecast 270 also includes study duration 1015, which is an amount of time during which the clinical trial study is expected to be completed. Milestones 1005 can be defined for a number of selected high-level or summary tasks that each include a number of tasks and/or sub-tasks, where the corresponding expected date 1010 includes the amount of time during which the tasks and/or sub-tasks are expected to be completed. The total number of milestones 1005 is less than the total number of tasks included in the effort forecast. Milestones 1005 can be selected by a system administrator and/or a user as part of the operational parameters of the data model.

Other operational parameters can be involved in generating timeline forecast 270. For example, although a number of tasks are assigned to a given resource, the total number of hours involved in performing the tasks likely could not be accomplished by a single employee (or else the study might take on the order of years to complete, rather than on the order of months). Using a number of available hours for a single full-time employee over a period of time (such as a year), forecast output module 250 can calculate how many employees are needed to perform that particular task (e.g., dividing the extended unit hours 830 of the task by the number of available hours for an employee). The number of available hours can be stored by a system administrator as an operational parameter of the data model in resource information. Thus, the total length of time needed to perform that particular task may be different from the extended unit hours 830 of the task. For example, parts of the task may be performed in parallel, which shortens the task completion time (e.g., move up the expected date 1010), while other issues, such as vacation time, may result in delays and lengthen the task completion time (e.g., delay or push back the expected date 1010). Other operational parameters can be used to estimate dates of timeline forecast 270, such as an enrollment rate, site approval schedules for various countries, estimated amount of time expected to obtain site approval for a site, number of sites that need approval, expected time to perform data entry of CRF data and compile reports based on the CRF data, and the like.

Forecast output module 250 is also configured to provide timeline forecasts at various levels. For example, a high-level timeline forecast can provide a summary of a few high-level initiation and completion dates of the study, such as when the various phases of the study will start and end. Low-level timeline forecasts can include more granularity by displaying additional details in the summary of dates to implement the study. For example, the timeline forecast can break down the dates of the phases into initiation and completion dates for a number of tasks of each phase (as illustrated in FIG. 10). Thus, the sponsor or user can use the timeline forecast to anticipate the time needed to implement the study and make decisions about how the study will be implemented. For example, the timeline forecast can be used to begin negotiations with an investigator to implement the study, where timeline forecast can be used to highlight where assumptions of the sponsor and investigator differ (e.g., the investigator and sponsor might have different ideas of the amount of time needed to implement a particular phase of the study).

Forecast output module 250 can communicate a visual representation of timeline forecast 270 to viewer UI module 210, which in turn communicates the visual representation to a user interface 115 for display to a user. Forecast output module 250 can store timeline forecast 270 in network storage 160 as clinical trial study data 170, where timeline forecast 270 is associated (in clinical trial study data 170) with the data model object that represents the particular study.

Figure 11A:
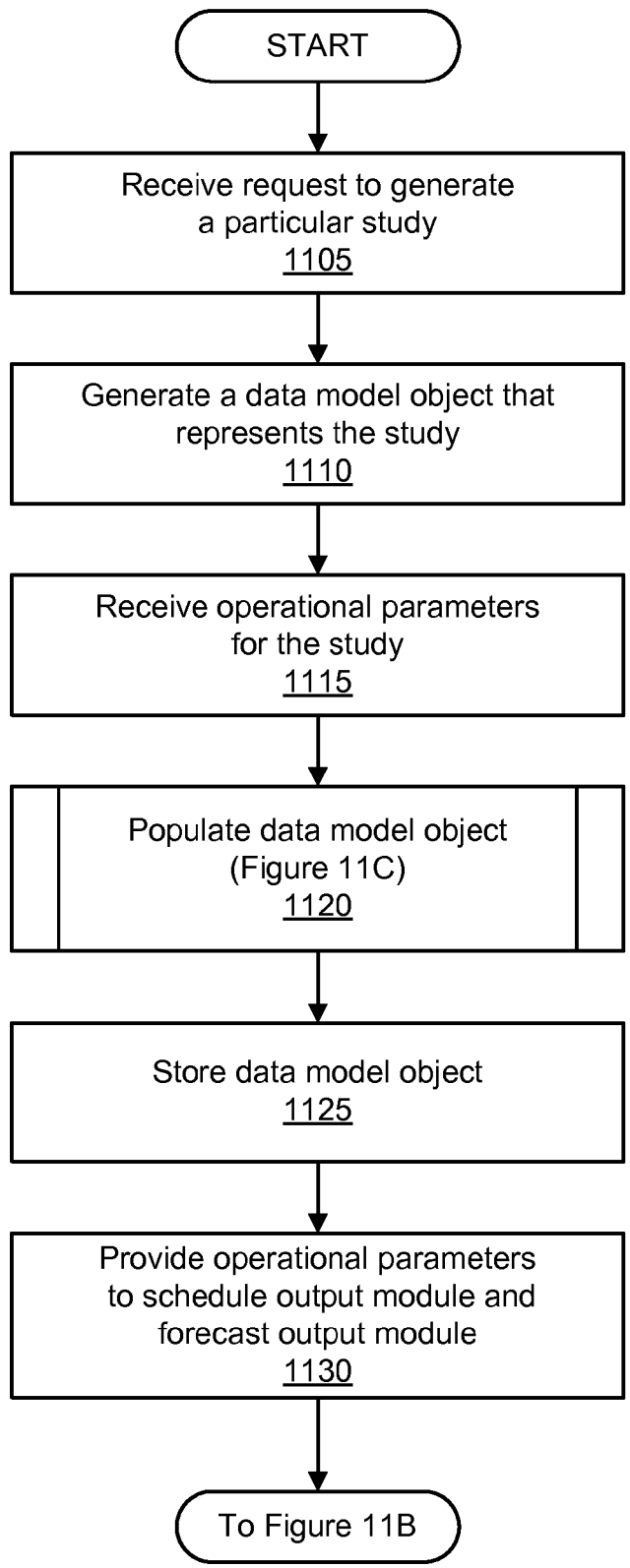
FIGS. 11A, 11B, and 11C are flowcharts illustrating an example process implemented by a forecasting engine, according to one embodiment.
Figure 11B:
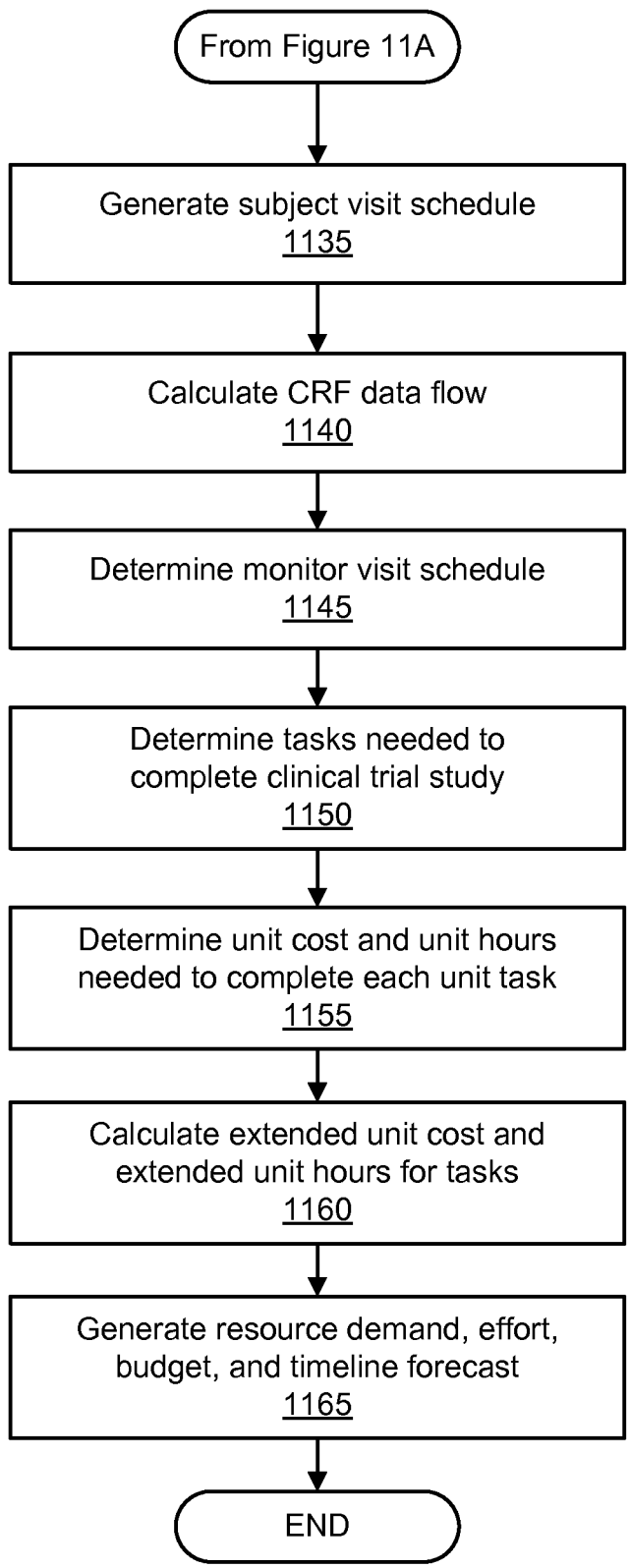

FIGS. 11A and 11B are flowcharts illustrating an example process implemented by a forecasting engine. The process illustrated in FIGS. 11A and 11B can be implemented in response to a user request (e.g., a user request received from a user interface) for generating a study (e.g., generating a data model object representing the study), generating a schedule (e.g., a subject visit schedule and/or a monitor visit schedule) and/or a forecast (e.g., a resource demand, effort, cost, and/or timeline forecast) and/or upon receiving data used to complete calculations of effort, resource demand, cost and/or time (e.g., receiving updated cost estimates associated with various tasks required to complete or update the forecast generation). The process illustrated in FIGS. 11A and 11B can be cooperatively implemented by a user input module, a study output module, and a forecast output module of a forecasting engine.

The process begins at operation 1105 of FIG. 11A, where the user input module receives a request to generate a particular study from a user interface. In response, the process continues to operation 1110, where user input module generates a data model object that represents the study, using the clinical trial study data model as a template. The process continues to operation 1115, where the user input module receives operational parameters for the particular study from a user interface. The operational parameters are user-specified values that describe the scope of the clinical trial study. The process continues to operation 1120, where the user input module populates the data model object. Operation 1120 is further described in connection with FIG. 11C. The process continues to operation 1125, where user input module stores the data model object that includes the operational parameters as part of clinical trial study data in network storage. The process continues to operation 1130, where the user input module provides the operational parameters (e.g., individually or as part of the data model object) to the schedule output module and the forecast output module. The process then continues to FIG. 11B.

The process continues to operation 1135 of FIG. 11B, where the schedule output module generates a master subject visit schedule for the testing phase of the study, based on the operational parameters of the data model. The schedule output module can determine a number of subject group visit schedules that are included in the master subject visit schedule. The process continues to operation 1140, where the schedule output module calculates CRF data flow over the testing phase, based on the master subject visit schedule and operational parameters of the data model. The process continues to operation 1145, where the schedule output module determines a master monitor visit schedule, based on the CRF data flow. The schedule output module can also determine multiple monitor visit schedules for a given monitor and/or for a number of monitors. The schedule output module can also provide generated schedules to the user input module for display to a user on a user interface. Although not shown, the schedule output module also stores the generated information (e.g., a master subject visit schedule, a number of subject group visit schedules, CRF data flow, master monitor visit schedule, and a number of monitor visit schedules) as part of clinical trial study data in network storage, where such generated information is associated with the data model object.

The process continues to operation 1150, where the forecast output module determines a number of tasks that are needed to complete the clinical trial study, based on the operational parameters of the data model. For example, forecast output module can consult clinical trial study data for resource and task information to determine a number of known resources and/or tasks, where a user can specify which resources and tasks are needed to implement the clinical trial study (e.g., a particular treatment or phase of a study requires a particular resource, as specified in the operational parameters). The forecast output module can identify a number of resources that are needed to implement the study as specified by the user (e.g., identify the resources from a master list of resources stored in network storage) and can associate those identified resources with the data model object in clinical trial study data (e.g., associate a list of identified resources with the data model object). Similarly, the forecast output module can identify a number of tasks that are needed to implement the study, where the tasks can be identified due to an existing association between the task and one of the resources that were identified, or can be identified by the user (e.g., a particular treatment or phase of a study requires a particular task, as specified in the operational parameters). The forecast output module can also associate those tasks with the data model object in network storage (e.g., associate a list of identified tasks with the data model object), and can also associate those tasks with a number of resources that should perform the tasks (e.g., some tasks may have new associations created, or some tasks may not have an existing association with a resource).

The process continues to operation 1155, where the forecast output module determines a unit cost and a number of unit hours that are needed to complete a unit task, based on operational parameters. For example, forecast output module can consult clinical trial study data for resource and task information to determine the unit cost and unit hours associated with each unit task (e.g., each identified task on a list of identified tasks that is associated with the data model object). The process continues to operation 1160, where the forecast output module calculates the extended unit cost and extended unit hours for tasks, based on the unit cost and unit hours and/or operational parameters of the data model. The process continues to operation 1165, where the forecast output module generates one or more forecasts that include a resource demand forecast, an effort forecast, a budget forecast, and a timeline forecast. The forecast output module can also provide generated forecasts to the user input module for display to a user on a user interface. The process then ends.

Figure 11C:
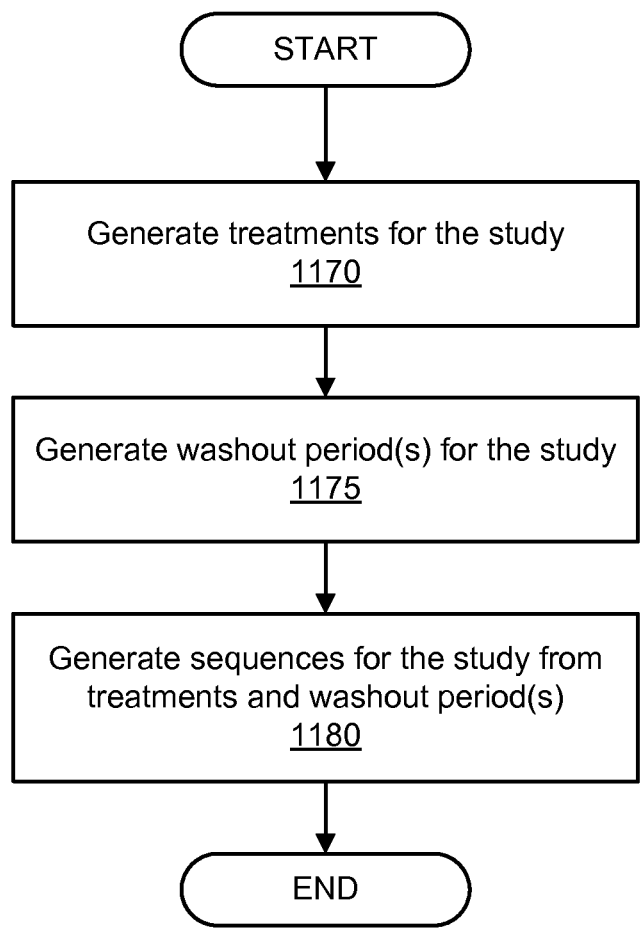

FIG. 11C further illustrates a flowchart of an example populating process of a data model object implemented by a forecasting engine. The process begins at operation 1170, where the user input module generates a number of treatments for the particular study, according to the operational parameters. As discussed above, the operational parameters include a number of specified values that describe the treatments that a user wishes to include in the study. Using the treatment entity of the clinical trial study data model, the user input module generates a number of instances of treatment entity, where each treatment instance represents a given treatment that a user wishes to include in the study. The user input module stores the treatment instances in the data model object that represents the particular study (e.g., populates the data model object with the treatment instances), where each treatment instance includes operational parameters that relate to the represented treatment.

The process continues to operation 1175, where the user input module generates one or more washout periods for the study, according to the operational parameters. As discussed above, the operation parameters include a number of specified values that describe at least one washout period that a user wishes to include in the study. Using the washout period entity of the clinical trial study data model, the user input module generates one or more instances of washout period entity, where each washout period instance represents a given washout period that a user wishes to include in the study. The user input module stores the one or more washout period instances in the data model object that represents the particular study (e.g., populates the data model object with the washout period instances), where each washout period includes operational parameters that relate to the represented washout period.

The process continues to operation 1180, where the user input module generates a number of sequences for the study from the treatment instances and one or more washout period instances (which can have the same or different washout period lengths), according to the operational parameters. As described above, the operation parameters include a number of specified values that describe a study protocol design and (optionally) a number of selected treatments that a user wishes to include in the study. Using the sequence entity of the clinical trial study data model, the user input module generates a number of instances of sequence entity, where each generated sequence instance represents a given sequence that could be included in the study (which may be a greater number of sequences than the number selected by the user to be included in the study). Each sequence instance includes a combination of treatment instances (such as one or more treatment instances that represent test treatments and at least one treatment instance that represents a control treatment) and one or more washout period instances.

Sequence instances can be automatically generated by user input module according to the study protocol design specified in the operational parameters. A user can also identify a number of generated sequence instances to be included in the study, which can be less than the total number of generated sequence instances. In some embodiments, the user input module randomly selects the number of sequence instances from the generated sequence instances, which are then included in the study. Sequence instances can also be manually generated by a user. In some embodiments, the user can select each treatment instance and washout period instance to be included in a given sequence instance via the user interface (e.g., viewer UI module provides a number of treatment instances generated by the user input module, where the user can select each treatment instance to be included in the sequence instance, such as via a UI button or other element to indicate the selection). The user input module can also verify that the manually generated sequence instances satisfy the study protocol design specified in the operational parameters. The user input module stores the sequence instances in the data model object that represents the particular study (e.g., populates the data model object with the sequence instances), where each sequence instance includes operational parameters that relate to the represented sequence. The process then ends.

An Example Computing and Network Environment

As shown above, the present invention can be implemented using a variety of computer systems and networks. An example of one such computing and network environment is described below with reference to FIGS. 12 and 13.

Figure 12:
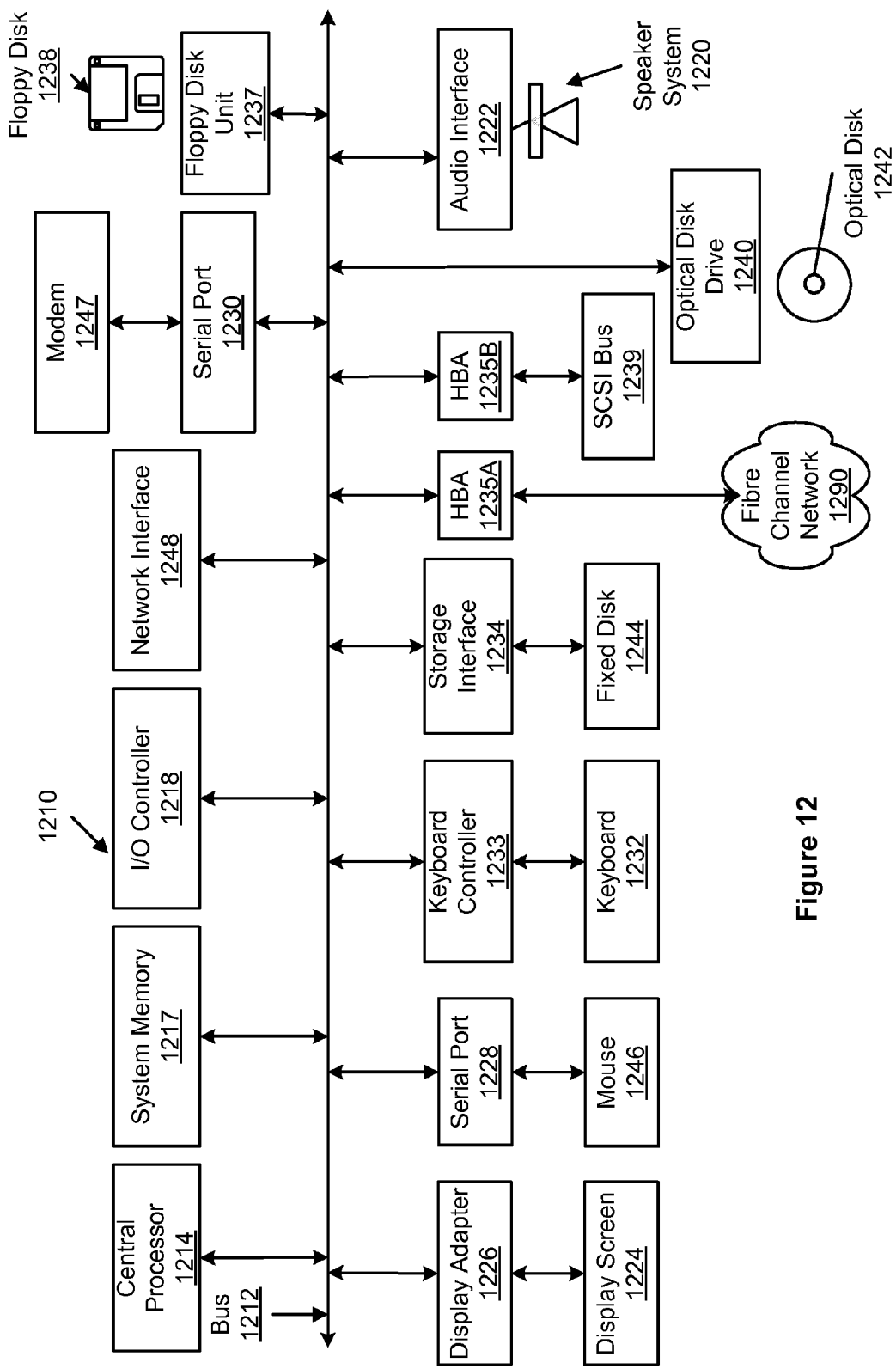
FIG. 12 is a simplified block diagram of an example computer system suitable for implementing aspects of the present disclosure, according to one embodiment.

FIG. 12 depicts a block diagram of a computer system 1210 suitable for implementing aspects of the present invention (e.g., clients 110 and/or server 120). Computer system 1210 includes a bus 1212 which interconnects major subsystems of computer system 1210, such as a central processor 1214, a system memory 1217 (typically RAM, but which may also include ROM, flash RAM, or the like), an input/output controller 1218, an external audio device, such as a speaker system 1220 via an audio output interface 1222, an external device, such as a display screen 1224 via display adapter 1226, serial ports 1228 and 1230, a keyboard 1232 (interfaced with a keyboard controller 1233), a storage interface 1234, a floppy disk drive 1237 operative to receive a floppy disk 1238, a host bus adapter (HBA) interface card 1235A operative to connect with a Fibre Channel network 1290, a host bus adapter (HBA) interface card 1235B operative to connect to a SCSI bus 1239, and an optical disk drive 1240 operative to receive an optical disk 1242. Also included are a mouse 1246 (or other point-and-click device, coupled to bus 1212 via serial port 1228), a modem 1247 (coupled to bus 1212 via serial port 1230), and a network interface 1248 (coupled directly to bus 1212).

Bus 1212 allows data communication between central processor 1214 and system memory 1217, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components. Applications resident with computer system 1210 are generally stored on and accessed via a computer-readable medium, such as a hard disk drive (e.g., fixed disk 1244), an optical drive (e.g., optical drive 1240), a floppy disk unit 1237, or other storage medium. Additionally, applications can be in the form of electronic signals modulated in accordance with the application and data communication technology when accessed via network modem 1247 or interface 1248.

Storage interface 1234, as with the other storage interfaces of computer system 1210, can connect to a standard computer-readable medium for storage and/or retrieval of information, such as a fixed disk drive 1244. Fixed disk drive 1244 may be a part of computer system 1210 or may be separate and accessed through other interface systems. Modem 1247 may provide a direct connection to a remote server via a telephone link or to the Internet via an internet service provider (ISP). Network interface 1248 may provide a direct connection to a remote server via a direct network link to the Internet via a POP (point of presence). Network interface 1248 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on). Conversely, all of the devices shown in FIG. 12 need not be present to practice the present invention. The devices and subsystems can be interconnected in different ways from that shown in FIG. 12. The operation of a computer system such as that shown in FIG. 12 is readily known in the art and is not discussed in detail in this application. Code to implement the present invention can be stored in computer-readable storage media such as one or more of system memory 1217, fixed disk 1244, optical disk 1242, or floppy disk 1238. The operating system provided on computer system 1210 may be MS-DOS®, MS-WINDOWS®, OS/2®, UNIX®, Linux®, or another known operating system.

Moreover, regarding the signals described herein, those skilled in the art will recognize that a signal can be directly transmitted from a first block to a second block, or a signal can be modified (e.g., amplified, attenuated, delayed, latched, buffered, inverted, filtered, or otherwise modified) between the blocks. Although the signals of the above described embodiment are characterized as transmitted from one block to the next, other embodiments of the present invention may include modified signals in place of such directly transmitted signals as long as the informational and/or functional aspect of the signal is transmitted between blocks. To some extent, a signal input at a second block can be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

Figure 13:
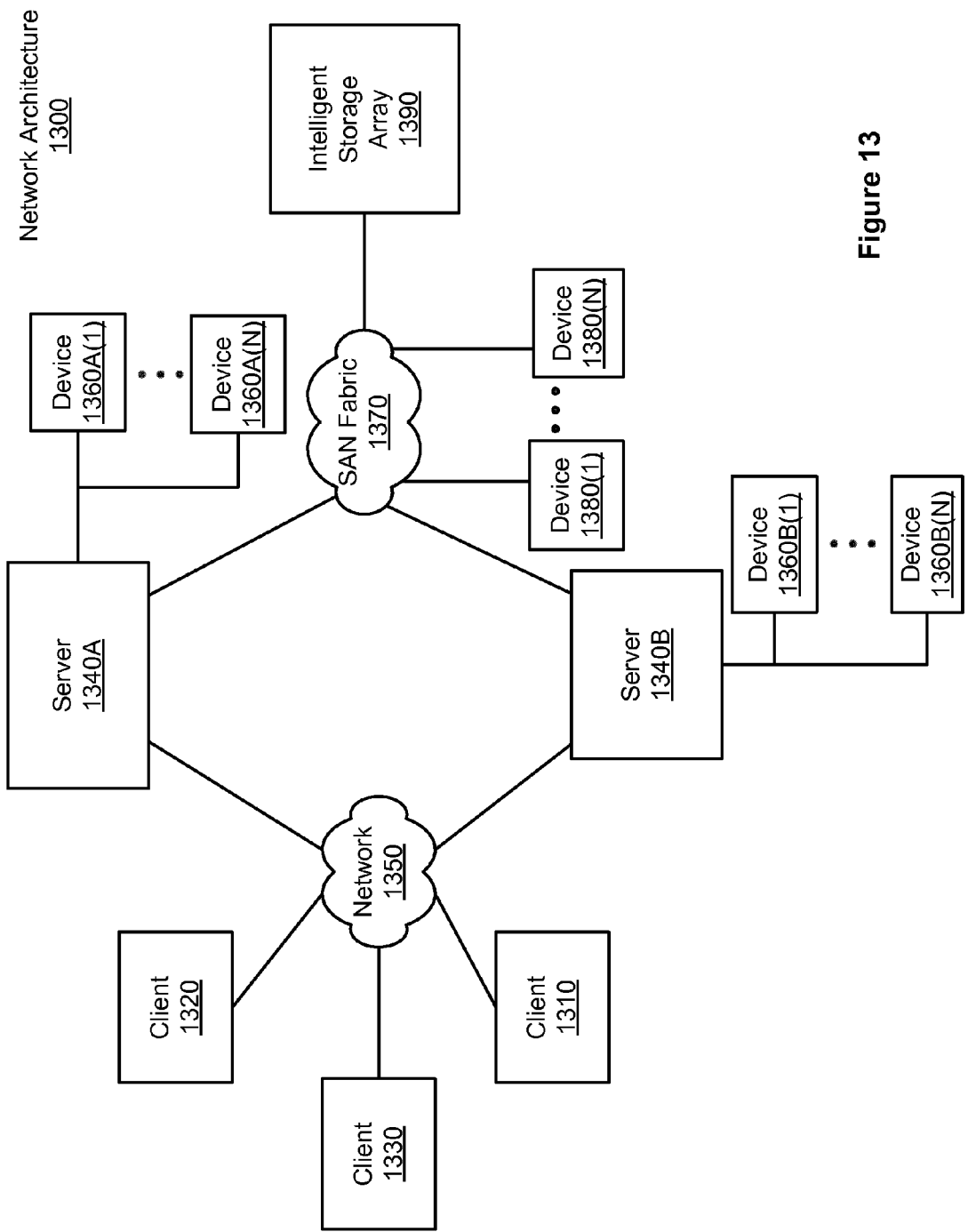
FIG. 13 is a simplified block diagram of a network architecture suitable for implementing aspects of the present disclosure, according to one embodiment.

FIG. 13 is a block diagram depicting a network architecture 1300 in which client systems 1310, 1320 and 1330, as well as storage servers 1340A and 1340B (any of which can be implemented using computer system 1210), are coupled to a network 1350. Storage server 1340A is further depicted as having storage devices 1360A(1)-(N) directly attached, and storage server 1340B is depicted with storage devices 1360B(1)-(N) directly attached. Storage servers 1340A and 1340B are also connected to a SAN fabric 1370, although connection to a storage area network is not required for operation of the invention. SAN fabric 1370 supports access to storage devices 1380(1)-(N) by storage servers 1340A and 1340B, and so by client systems 1310, 1320 and 1330 via network 1350. Intelligent storage array 1390 is also shown as an example of a specific storage device accessible via SAN fabric 1370.

With reference to computer system 1210, modem 1247, network interface 1248 or some other method can be used to provide connectivity from each of client computer systems 1310, 1320 and 1330 to network 1350. Client systems 1310, 1320 and 1330 are able to access information on storage server 1340A or 1340B using, for example, a web browser or other client software (not shown). Such a client allows client systems 1310, 1320 and 1330 to access data hosted by storage server 1340A or 1340B or one of storage devices 1360A(1)-(N), 1360B(1)-(N), 1380(1)-(N) or intelligent storage array 1390. FIG. 13 depicts the use of a network such as the Internet for exchanging data, but the present invention is not limited to the Internet or any particular network-based environment.

Other Embodiments

The present invention is well adapted to attain the advantages mentioned as well as others inherent therein. While the present invention has been depicted, described, and is defined by reference to particular embodiments of the invention, such references do not imply a limitation on the invention, and no such limitation is to be inferred. The invention is capable of considerable modification, alteration, and equivalents in form and function, as will occur to those ordinarily skilled in the pertinent arts. The depicted and described embodiments are examples only, and are not exhaustive of the scope of the invention.

The foregoing describes embodiments including components contained within other components (e.g., the various elements shown as components of computer system 1210). Such architectures are merely examples, and, in fact, many other architectures can be implemented which achieve the same functionality. In an abstract but still definite sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality.

The foregoing detailed description has set forth various embodiments of the present invention via the use of block diagrams, flowcharts, and examples. It will be understood by those within the art that each block diagram component, flowchart step, operation and/or component illustrated by the use of examples can be implemented, individually and/or collectively, by a wide range of hardware, software, firmware, or any combination thereof, including the specialized system illustrated in FIG. 1.

The present invention has been described in the context of fully functional computer systems; however, those skilled in the art will appreciate that the present invention is capable of being distributed as a program product in a variety of forms, and that the present invention applies equally regardless of the particular type of computer-readable media used to actually carry out the distribution. Examples of computer-readable media include computer-readable storage media, as well as media storage and distribution systems developed in the future.

The above-discussed embodiments can be implemented by software modules that perform one or more tasks associated with the embodiments. The software modules discussed herein may include script, batch, or other executable files. The software modules may be stored on a machine-readable or computer-readable storage media such as magnetic floppy disks, hard disks, semiconductor memory (e.g., RAM, ROM, and flash-type media), optical discs (e.g., CD-ROMs, CD-Rs, and DVDs), or other types of memory modules. A storage device used for storing firmware or hardware modules in accordance with an embodiment of the invention can also include a semiconductor-based memory, which may be permanently, removably or remotely coupled to a microprocessor/memory system. Thus, the modules can be stored within a computer system memory to configure the computer system to perform the functions of the module. Other new and various types of computer-readable storage media may be used to store the modules discussed herein.

The above description is intended to be illustrative of the invention and should not be taken to be limiting. Other embodiments within the scope of the present invention are possible. Those skilled in the art will readily implement the steps necessary to provide the structures and the methods disclosed herein, and will understand that the process parameters and sequence of steps are given by way of example only and can be varied to achieve the desired structure as well as modifications that are within the scope of the invention. Variations and modifications of the embodiments disclosed herein can be made based on the description set forth herein, without departing from the scope of the invention.

Consequently, the invention is intended to be limited only by the scope of the appended claims, giving full cognizance to equivalents in all respects.

What is claimed is:

1. A method, performed by a computer that includes at least a processor and a memory, the method comprising:
   generating, by the processor, a data model object that is stored in the memory, wherein the data model object comprising
      a treatment entity identifying a plurality of treatments for a clinical trial study, wherein
         each of the plurality of treatments is based on a first subset of operational parameters;
      a sequence entity identifying a plurality of sequences for the clinical trial study, wherein
         each of the plurality of sequences is based on a second subset of the operational parameters, wherein
            the second subset comprises a washout period parameter representing a washout period associated with each of the sequences, and
         each sequence of the plurality of sequences comprises a combination of ones of the plurality of treatments;
   assigning, by the processor using the data model object, a plurality of subject groups to each of the plurality of sequences, wherein
      one subject group of the plurality of subject groups is respectively assigned to one sequence of the plurality of sequences,
      the one sequence is scheduled to be administered to subjects of the one subject group during the clinical trial study, and
      the one sequence is determined, at least in part, based on the washout period parameter associated with the one sequence;
   generating in a data structure, by the processor, a subject visit schedule for the plurality of sequences and the assigned subject groups, wherein the subject visit schedule indicates a plurality of subject visits scheduled for the one subject group assigned to the one sequence; and
   transmitting, by the processor via network communication, the data structure including the subject visit schedule to a user interface to display the subject visit schedule on a device to assist a user to schedule the plurality of treatments according to the subject visit schedule.

2. The method of claim 1, wherein
   the clinical trial study implements a cross-over testing design, and each sequence comprises at least one test treatment and at least one control treatment.

3. The method of claim 1, further comprising:
calculating a data flow based on a plurality of subject visit schedules, wherein
the data flow indicates when subject data is available for collection; and
determining a monitor visit schedule based on the data flow, wherein
the monitor visit schedule indicates a plurality of monitor visits scheduled for collection of the subject data.

4. The method of claim 1, further comprising:
associating a plurality of tasks with the clinical trial study, wherein
the plurality of tasks are configured to implement the clinical trial study; and
assigning the plurality of tasks to a plurality of resources, wherein
the resources are assigned to perform the plurality of tasks.

5. The method of claim 4, further comprising:
generating a resource demand forecast, wherein
the resource demand forecast comprises
a list of the plurality of resources, and
a sub-list for each subset of the plurality of tasks that is assigned to each of the plurality of resources.

6. The method of claim 4, further comprising:
generating an effort forecast, wherein
the effort forecast comprises
a list of the plurality of tasks,
a respective cost of each task of the plurality of tasks, wherein the respective cost is incurred to complete the each task, and
a respective amount of time of each task, wherein the each task is estimated to be completed within the respective amount of time.

7. The method of claim 4, further comprising:
generating a budget forecast, wherein
the budget forecast comprises
a respective periodic cost of each task of the plurality of tasks, wherein the respective periodic cost is incurred to complete the each task during each of a plurality of periods, and
a total periodic cost of the plurality of tasks, wherein the total periodic cost is incurred to complete the plurality of tasks during each of the plurality of periods.

8. The method of claim 4, further comprising:
generating a timeline forecast, wherein
the timeline forecast comprises a plurality of milestones and a corresponding plurality of dates, and
the milestones indicate selected occurrences of tasks associated with the clinical trial study.

9. A non-transitory computer readable storage medium configured to store program instructions that, when executed on a processor, are configured to cause the processor to:
generate a data model object and storing the data model object in a memory, wherein the data model object comprising
a treatment entity identifying a plurality of treatments for a clinical trial study, wherein
each of the plurality of treatments is based on a first subset of the operational parameters;
a sequence entity identifying a plurality of sequences for the clinical trial study, wherein
each of the plurality of sequences is based on a second subset of the operational parameters, wherein the second subset comprises a washout period parameter representing a washout period associated with each of the sequences, and
each sequence of the plurality of sequences comprises a combination of ones of the plurality of treatments;
assign, by the processor using the data model object, a plurality of subject groups to each of the plurality of sequences, wherein
one subject group of the plurality of subject groups is respectively assigned to one sequence of the plurality of sequences,
the one sequence is scheduled to be administered to subjects of the one subject group during the clinical trial study, and
the one sequence is determined, at least in part, based on the washout period parameter associated with the one sequence;
generate in a data structure, by the processor, a subject visit schedule for the plurality of sequences and the assigned subject groups, wherein the subject visit schedule indicates a plurality of subject visits scheduled for the one subject group assigned to the one sequence; and
transmit, by the processor via network communication, the data structure including the subject visit schedule to a user interface to display the subject visit schedule on a device to assist a user to schedule the plurality of treatments according to the subject visit schedule.

10. The non-transitory computer readable storage medium of claim 9, further comprises stored program instructions that, when executed by the processor, are configured to cause the processor to:
calculate a data flow based on a plurality of subject visit schedules, wherein
the data flow indicates when subject data is available for collection; and
determine a monitor visit schedule based on the data flow, wherein
the monitor visit schedule indicates a plurality of monitor visits scheduled for collection of the subject data.

11. The non-transitory computer readable storage medium of claim 9, further comprises stored program instructions that, when executed by the processor, are configured to cause the processor to:
associate a plurality of tasks with the clinical trial study, wherein
the plurality of tasks are configured to implement the clinical trial study; and
assign the plurality of tasks to a plurality of resources, wherein
the resources are assigned to perform the plurality of tasks.

12. The non-transitory computer readable storage medium of claim 11, further comprises stored program instructions that, when executed on the processor, are configured to cause the processor to:
generate a resource demand forecast, wherein
the resource demand forecast comprises
a list of the plurality of resources, and
a sub-list for each subset of the plurality of tasks that is assigned to each of the plurality of resources.

13. The non-transitory computer readable storage medium of claim 11, further comprises stored program instructions that, when executed on the processor, are configured to cause the processor to:
generate an effort forecast, wherein
the effort forecast comprises
a list of the plurality of tasks,
a respective cost of each task of the plurality of tasks, wherein the respective cost is incurred to complete the each task, and
a respective amount of time of each task, wherein the each task is estimated to be completed within the respective amount of time.

14. An apparatus comprising:
a computer including at least a processor for executing instructions; and
a memory coupled to the processor and configured with stored instructions executable by the processor to:
generate a data model object and storing the data model object in the memory, wherein the data model object comprising
a treatment entity identifying a plurality of treatments for a clinical trial study, wherein each of the plurality of treatments is based on a first subset of the operational parameters;
a sequence entity identifying a plurality of sequences for the clinical trial study, wherein
each of the plurality of sequences is based on a second subset of the operational parameters, wherein the second subset comprises a washout period parameter representing a washout period associated with each of the sequences, and
each sequence of the plurality of sequences comprises a combination of ones of the plurality of treatments;
use the data model to assign a plurality of subject groups to each of the plurality of sequences, wherein
one subject group of the plurality of subject groups is respectively assigned to one sequence of the plurality of sequences,
the one sequence is scheduled to be administered to subjects of the one subject group during the clinical trial study, and
the one sequence is determined, at least in part, based on the washout period parameter associated with the one sequence;
generate in a data structure, by the processor, a subject visit schedule for the plurality of sequences and the assigned subject groups, wherein the subject visit schedule indicates a plurality of subject visits scheduled for the one subject group assigned to the one sequence; and
transmit, by the processor via network communication, the data structure including the subject visit schedule to a user interface to display the subject visit schedule on a device to assist a user to schedule the plurality of treatments according to the subject visit schedule.

15. The apparatus of claim 14, wherein the memory further includes stored instructions executable by the processor to cause the processor to:
generate a subject visit schedule for the one sequence of the set of the plurality of sequences, wherein
the subject visit schedule indicates a plurality of subject visits scheduled for the subject group assigned to the one sequence.

16. The apparatus of claim 14, wherein the memory further includes stored instructions executable by the processor to cause the processor to:
calculate a data flow based on a plurality of subject visit schedules, wherein
the data flow indicates when subject data is available for collection; and
determine a monitor visit schedule based on the data flow, wherein
the monitor visit schedule indicates a plurality of monitor visits scheduled for collection of the subject data.

17. The apparatus of claim 14, wherein the memory further includes stored instructions executable by the processor to cause the processor to:
associate a plurality of tasks with the clinical trial study, wherein
the plurality of tasks are configured to implement the clinical trial study; and
assign the plurality of tasks to a plurality of resources, wherein
the resources are assigned to perform the plurality of tasks.

18. The apparatus of claim 17, wherein the memory further includes stored instructions executable by the processor to cause the processor to generate at least one of
a resource demand forecast, wherein
the resource demand forecast comprises
a list of the plurality of resources, and
a sub-list for each subset of the plurality of tasks that is assigned to each of the plurality of resources, and
an effort forecast, wherein
the effort forecast comprises
a list of the plurality of tasks,
a respective cost of each task of the plurality of tasks, wherein the respective cost is incurred to complete the each task, and
a respective amount of time of each task, wherein the each task is estimated to be completed within the respective amount of time.

* * * * *